United States Patent
Chen et al.

(10) Patent No.: US 8,563,719 B2
(45) Date of Patent: Oct. 22, 2013

(54) PROCESS AND INTERMEDIATES FOR PREPARING LAPATINIB

(75) Inventors: Yung-Fa Chen, Tainan (TW); Julian Paul Henschke, Tainan (AU); Yuanlian Liu, Kunshan (CN); Guodong Chu, Jiaxiang (CN); Xiaoheng Zhang, Changshu (CN)

(73) Assignee: Scinopharm Taiwan, Ltd., Tainan (TW)

( * ) Notice: Subject to any disclaimer, the term of this patent is extended or adjusted under 35 U.S.C. 154(b) by 0 days.

(21) Appl. No.: 13/582,875

(22) PCT Filed: Mar. 23, 2011

(86) PCT No.: PCT/CN2011/000493
§ 371 (c)(1),
(2), (4) Date: Sep. 5, 2012

(87) PCT Pub. No.: WO2011/116634
PCT Pub. Date: Sep. 29, 2011

(65) Prior Publication Data

US 2013/0005971 A1    Jan. 3, 2013

Related U.S. Application Data

(60) Provisional application No. 61/316,425, filed on Mar. 23, 2010.

(51) Int. Cl.
*C07D 239/72*    (2006.01)
(52) U.S. Cl.
USPC .......................... 544/283; 544/287; 544/293

(58) Field of Classification Search
USPC .......................................... 544/283, 287, 293
See application file for complete search history.

(56) References Cited

U.S. PATENT DOCUMENTS

| 6,713,485 B2 | 3/2004 | Carter et al. |
| 6,727,256 B1 | 4/2004 | Carter et al. |
| 7,157,466 B2 | 1/2007 | McClure et al. |

FOREIGN PATENT DOCUMENTS

| AU | 2005203303 A1 | 8/2005 |
| WO | WO2006/066267 A2 | 6/2006 |
| WO | WO2009/042613 A1 | 4/2009 |
| WO | WO-2009/079541 A2 | 6/2009 |
| WO | WO-2010/017387 A2 | 2/2010 |

OTHER PUBLICATIONS

Organic Process Research & Development 2005, 9, 198-205.
Organic Process Research & Development 2003, 7, 733-742.
Petrov, K. G., Optimization and SAR for dual ErbB-1/ErbB-2 tyrosine kinase inhibition in 6-furanylquinazoline series, Bio-organic & Medicinal Chemistry Letters, Jun. 13, 2006, vol. 16, pp. 4686-4691.
Organic Process Research & Development 2009, 13, 429-433.
English Translation of Search Report of the Taiwan Counterpart Patent Application No. TW100109970, Dec. 18, 2012.

*Primary Examiner* — Andrew D Kosar
*Assistant Examiner* — John S Kenyon
(74) *Attorney, Agent, or Firm* — Enshan Hong; Kent H. Cheng; VLP Law Group LLP

(57) ABSTRACT

The present invention provides a process for making lapatinib and its pharmaceutically acceptable salt by use of new intermediates. A new process for obtaining a pharmaceutical form of lapatinib ditosylate monohydrate is also provided.

27 Claims, 11 Drawing Sheets

Peak List

| Pos.[°2Th.] | Height[cts] | FWHM[°2Th.] | d-spacing[Å] | Rel.Int.[%] |
|---|---|---|---|---|
| 4.3798 | 5074.54 | 0.1299 | 20.17560 | 50.76 |
| 6.6843 | 2259.70 | 0.1624 | 13.22397 | 22.60 |
| 8.8137 | 3798.22 | 0.1624 | 10.03325 | 38.00 |
| 12.6461 | 4342.42 | 0.2598 | 6.99999 | 43.44 |
| 13.3368 | 5607.24 | 0.2922 | 6.63896 | 56.09 |
| 15.3513 | 9587.54 | 0.1948 | 5.77199 | 95.91 |
| 15.5865 | 9996.55 | 0.1624 | 5.68542 | 100.00 |
| 16.6722 | 2714.03 | 0.2598 | 5.31754 | 27.15 |
| 17.7291 | 1828.12 | 0.2598 | 5.00286 | 18.29 |
| 21.0747 | 2319.15 | 0.2598 | 4.21561 | 23.20 |
| 24.3154 | 1718.33 | 0.2273 | 3.66062 | 17.19 |
| 25.1716 | 1964.46 | 0.1948 | 3.53801 | 19.65 |
| 25.7665 | 2882.31 | 0.3247 | 3.45766 | 28.83 |
| 26.6646 | 3507.49 | 0.2922 | 3.34320 | 35.09 |
| 27.2808 | 4881.92 | 0.2922 | 3.26908 | 48.84 |

FIG.3(continuous)

PROCESS AND INTERMEDIATES FOR PREPARING LAPATINIB

PRIORITY CLAIM

This is a U.S. national stage of application No. PCT/CN2011/000493, filed on Mar. 23, 2011. Priority is claimed on the following application: Country: U.S. Application No. 61/316,425, Filed: Mar. 23, 2010, the content of which is incorporated here by reference.

BACKGROUND OF THE INVENTION

1. Field of the Invention

The present invention is related to novel possesses of making lapatinib and lapatinib ditosylate, and novel intermediates thereof. Lapatinib has the structural formula (I) and chemical name N[3-chloro-4-[(3-fluorophenyl)methoxy]phenyl]-6-[5-[(2-methylsulfonylethylamino)methyl]-2-furyl]quinazolin-4-amine.

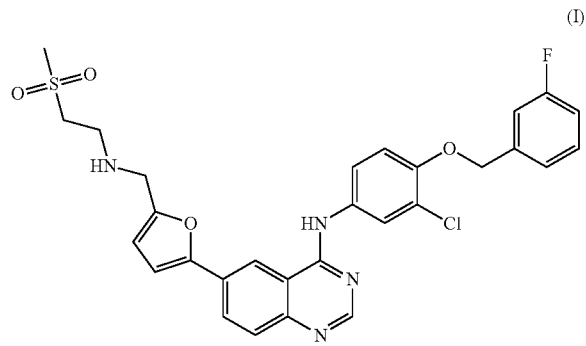 [SMILES: CS(=O)(=O)CCNCc1ccc(-c2ccc3ncnc(Nc4ccc(OCc5cccc(F)c5)c(Cl)c4)c3c2)o1]

(I)

2. Description of the Related Art

Lapatinib is a tyrosine kinase inhibitor that is used as an orally administered drug as its ditosylate salt to treat certain types of advanced or metastatic breast cancer and other solid tumors. Lapatinib ditosylate was approved by the FDA in 2007 and the EMEA in 2008 and is marketed by GlaxoSmithKline (GSK) under the trade name of Tykerb® in the USA and Tyverb® in Europe.

Lapatinib substance is claimed in U.S. Pat. No. 6,713,485 B2 and U.S. Pat. No. 6,727,256 B1 and lapatinib ditosylate and its crystalline forms are claimed in U.S. Pat. No. 7,157,466 B2. A synthesis of lapatinib that utilises a palladium mediated coupling of a substituted 4-anilino-6-iodo-quinazoline (II) with a 2-(tributylstannyl)furan (IIIa) is disclosed in U.S. Pat. No. 6,727,256 B1 and is also presented in U.S. Pat. No. 7,157,466 B2. In U.S. Pat. No. 7,157,466 B2 a second generation approach was disclosed that utilises a palladium catalysed coupling of a substituted 4-anilino-6-iodo-quinazoline (II) with furan-2-yl-boronic acids (IIIb). Following the palladium catalysed coupling reactions utilised in the two synthetic methods of U.S. Pat. No. 6,727,256 B1 and U.S. Pat. No. 7,157,466 B2, only one (U.S. Pat. No. 7,157,466 B2) or two (U.S. Pat. No. 6,727,256 B1 and U.S. Pat. No. 7,157,466 B2) synthetic modification of the structure are utilised before the lapatinib substance is provided (Scheme 1). The EMEA's Committee For Medicinal Products For Human Use (CHMP) has published guidelines titled Guideline On The Specification Limits For Residues Of Metal Catalysts Or Metal Reagents and recommendations are presented for oral exposure to metals, including palladium. For a drug being consumed in quantities not exceeding a 10 g daily dose, a limit of 10 ppm (parts per million) concentration of palladium in the drug substance is recommended. Given this, there is still an unmet need for an alternative synthetic method that can be used for preparation of lapatinib in which the palladium mediated coupling step is performed early in the synthetic route, thereby being capable to provide lapatinib and lapatinib tosylate or other salts with consistently low levels of palladium.

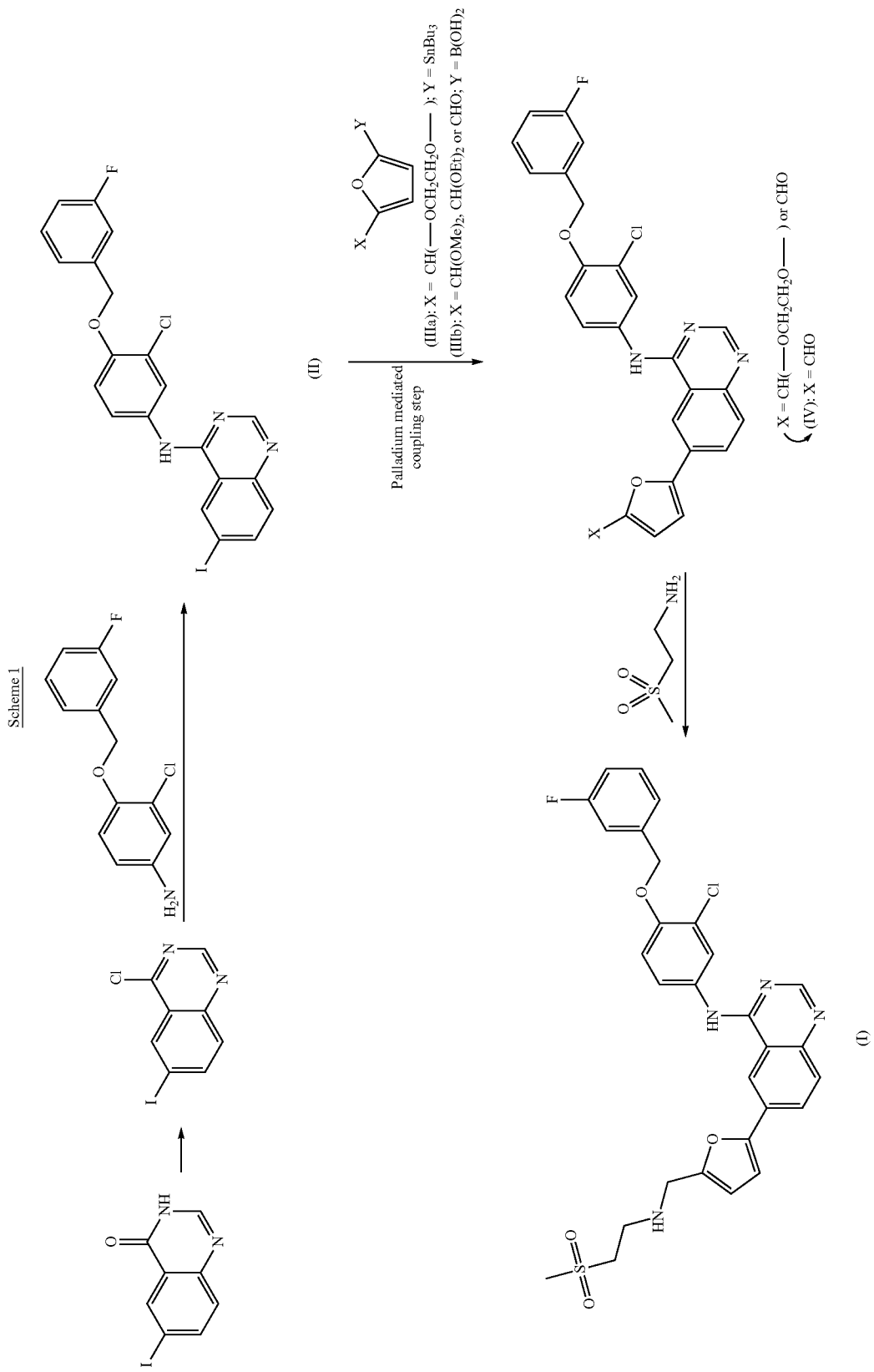

SUMMARY OF THE INVENTION

There are a number of ways that the levels of a metal, such as palladium, can be controlled in a drug substance through purging of the metal by treatment of the drug substance or its synthetic intermediates or both, including crystallisation, aqueous extraction, filtration through metal absorbent filter aids (Organic Process Research & Development 2005, 9, 198-205), precipitation of the metal from solution, chromatography, and treatment with metal scavenging reagents (Organic Process Research & Development 2003, 7, 733-742). By placing the palladium mediated coupling step downstream in the synthetic route, however, to take advantage of synthetic convergence, the opportunity to reduce the level of palladium in the drug substance is reduced. In contrast, however, by redesigning the synthetic route to move the palladium mediated coupling step upstream, further away from the drug substance, increases the opportunity to control the palladium level in the drug substance. Furthermore, by careful operational design (such as in a precipitation and crystallisation step), the palladium level in the intermediates can be consistently controlled. Given that there is a need, the present invention has addressed these two latter points and utilised them in a novel and efficient process for the manufacture of lapatinib and lapatinib ditosylate.

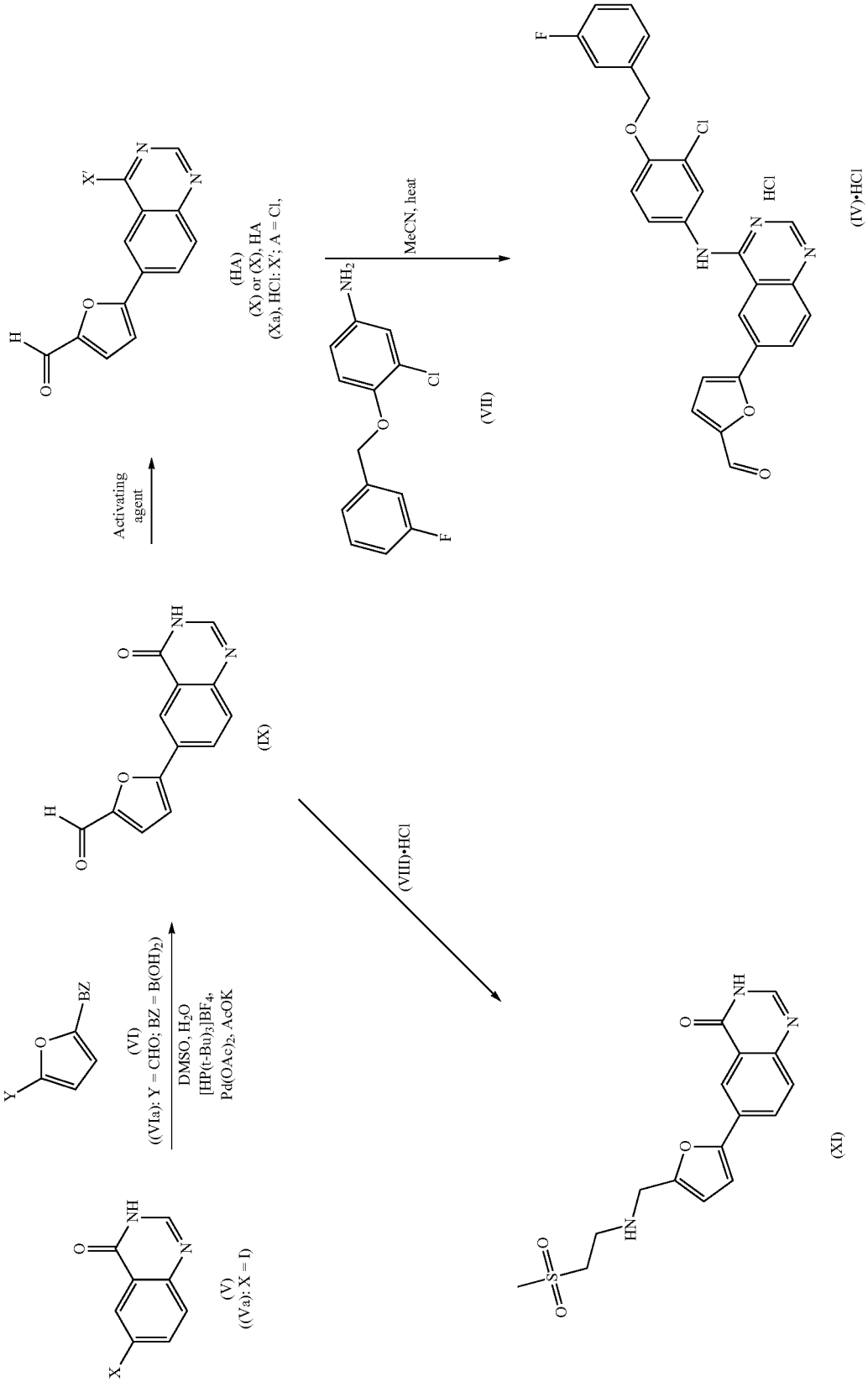

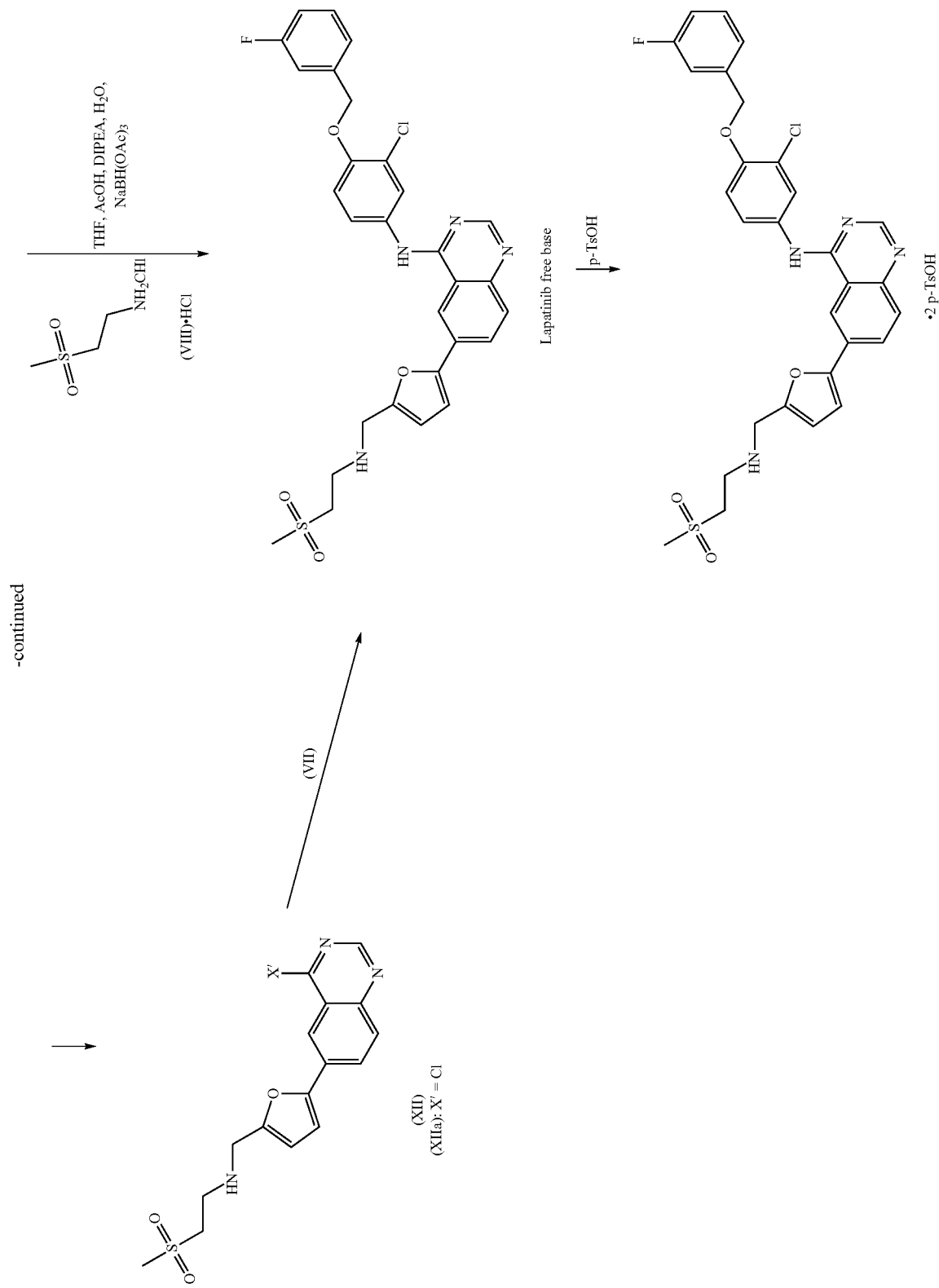

In contrast to the prior art methods disclosure in U.S. Pat. No. 6,727,256 B1 and U.S. Pat. No. 7,157,466 B2, the present invention has performed a transition metal catalysed coupling reaction at the most upstream point in the synthetic route based on the utilization of commercially available starting materials of formulae (Va) (6-iodoquinazolin-4(3H)-one) and (VIa) (5-formylfuran-2-ylboronic acid), or their analogues of formulae (V) and (VI), to provide a compound of formula (IX). Thus, in one aspect of the present invention, lapatinib is made from a novel compound of formula (IX) (Scheme 2).

In another aspect of the present invention, a lapatinib ditosylate monohydrate is prepared by crystallizing lapatinib ditosylate in a mixture of water, DMSO and MeCN.

In another aspect of the present invention, novel compound of formula (IX) is synthesized by the cross-coupling of commercially available compounds of formulae (Va) and (VIa), or their analogues of formulae (V) and (VI), in suitable solvents comprised of an organic solvent and water in the presence of a base and a catalyst formed from a transition metal and a ligand (scheme 3).

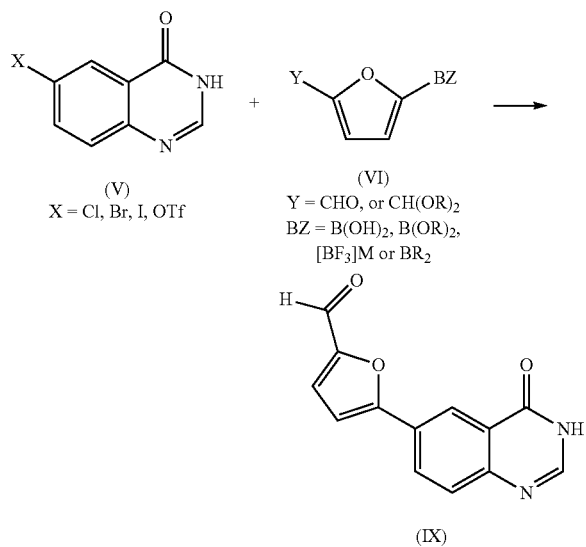

Scheme 3

(V)
X = Cl, Br, I, OTf (VI)
Y = CHO, or CH(OR)$_2$
BZ = B(OH)$_2$, B(OR)$_2$, [BF$_3$]M or BR$_2$ (IX)

The present invention provides a very convenient way to prepare the compound of formula (IX). By choice of an appropriate phosphine ligand and a palladium metal source only a small amount of catalyst is needed in the cross-coupling reaction of the compounds of formulae (Va) and (VIa) and this is applicable to large scale manufacturing of the compound of formula (IX). After the cross coupling reaction, the inorganic salt(s) and catalyst can be separated from the compound of formula (IX) by filtration or centrifugation. The compound of formula (IX) is then allowed to crystallise from the crude product mixture providing the compound of formula (IX) with high purity. Using this approach the compound of formula (IX) possesses an acceptable level of residual palladium metal that can be further reduced in concentration following further operations downstream providing the drug substance with very low concentrations of palladium metal. Preferably, the residual palladium concentration in the compound of formula (IX) is less than 300 ppm, more preferably less than 250 ppm, and most preferably less than 150 ppm. The residual palladium metal concentration in the lapatinib ditosylate that is prepared from the compound of formula (IX) prepared using the process of this invention is preferably less than 10 ppm, and is more preferably less than 5 ppm, and is most preferably less than 3 ppm.

In another aspect of the present invention, the use of alcohol solvents is avoided during the processing of intermediates that comprise salts with para-toluenesulfonic acid. Global regulatory authorities recommend/require drug substances to be manufactured with very low concentrations of genotoxic impurities (GTI) and potentially genotoxic impurities (PGI) to ensure safety to patients. Of the genotoxic impurities and potentially genotoxic impurities that can be present in drug substances arising from chemicals used in the manufacturing process, sulfonate esters (Organic Process Research & Development 2009, 13, 429-433) that can form from sulfonic acids and low molecular weight alcohols including MeOH, EtOH and i-PrOH are of concern. In WO 2010/017387 A2, the tosylate salt of compound of formula (IV) is treated with MeOH, or EtOH or i-PrOH at raised temperature for a period of time, before being filtered and dried. This operation provides the potential for methyl, ethyl and isopropyl sulfonate ester formation. Further, during the formation of compound of formula (IV) and its subsequent conversion into lapatinib ditosylate by reductive amination, we completely avoid the use of alcohols such as i-PrOH (which was reported in the reductive amination of tosylate salt of compound of formula (IV) in U.S. Pat. No. 7,157,466 B2) and instead conduct the reductive amination in the presence of water. One reported (Organic Process Research Development 2009 13 429-433) way to avoid sulfonate ester formation is by the inclusion of water in the process, and of course by the absence of alcohols contacting with the sulfonic acid. Although any sulfonate esters formed in cases such as in WO 2010/017387 A2 and U.S. Pat. No. 7,157,466 B2 might be destroyed in the downstream processing, the burden might be placed on the manufacturer by the regulatory authorities to prove this is the case. In the present process we avoid the contact of compound of formula (IV) with para-toluenesulfonic acid and with alcohols and instead use the hydrochloric acid salt of compound of formula (IV).

DETAILED DESCRIPTION OF THE PRESENTLY PREFERRED EMBODIMENTS

Figure 1:
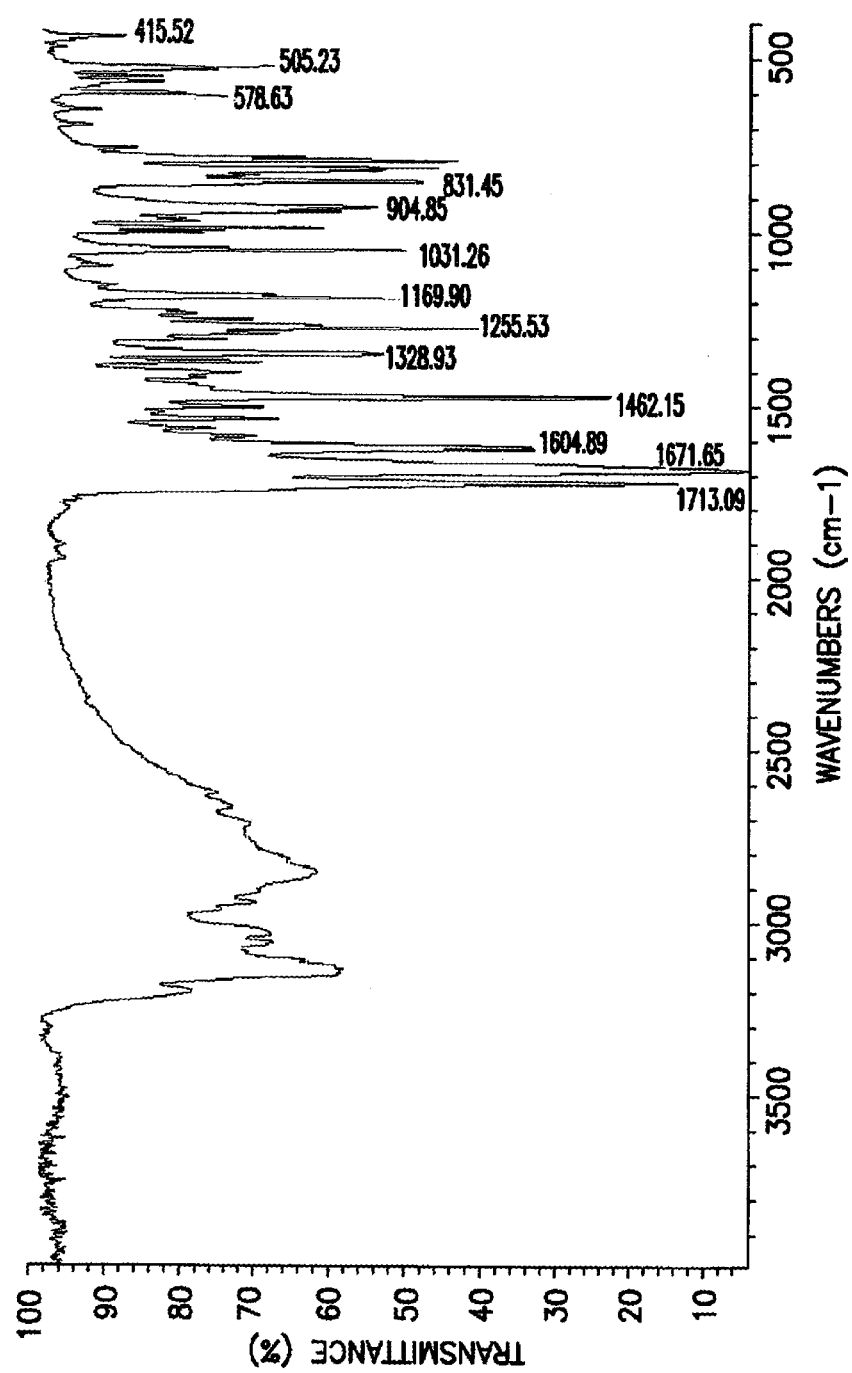
FIG. 1 shows the IR spectrum of the compound of formula (IX).

In one embodiment, lapatinib is produced by i) activating the compound of formula (IX)

ii) reacting the activated compound of formula (IX) with 3-chloro-4-(3-fluorobenzyloxy)aniline (VII) in a solvent with or without a base to produce the compound of formula (IV) or its salt, and

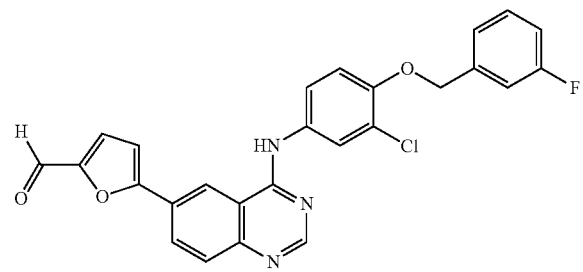

(IV)

iii) reductively aminating the compound of formula (IV) or its salt with 2-(methylsulfonyl)ethanamine (VIII) or its salt (e.g., (VIII).HCl) to provide lapatinib.

Lapatinib prepared in this way can be isolated or more preferably it can be directly converted into high purity lapatinib ditosylate salt, without isolation of the lapatinib, from the step iii) reaction product mixture by aqueous work-up and crystallisation in the presence of p-toluenesulfonic acid. The lapatinib ditosylate of this invention can be crystallised as a number of previously disclosed crystalline forms including a monohydrate form and Form 1 (as disclosed in U.S. Pat. No. 7,157,466 B2), and Form 2 (as disclosed in WO 2009/079541 A1).

In Step i), preferably, the compound of formula (IX) is activated to allow its facile reaction with the compound of formula (VII). In this way the compound of formula (IX) is converted to the compound of formula (X) (Scheme 4) where X' is a leaving group that can be displaced upon reaction with the compound of formula (VII). For example, X'=Cl, Br, I, OSO₂R, OPOCl₂, 6-benzotriazol-1-yloxy, [OP(NR₂)₃]BF₄ or PF₆, with a halogenating, sulfonating, phosphonylating or amide bond-forming reagent; wherein R is alkyl, aryl, heteroaryl; and wherein NR₂ is a dialkylamine or a heterocyclic ring including the N within the ring. When R is alkyl, it can be acyclic or it can be cyclic such that R₂ together forms a ring (such as a 5 or 6 membered ring).

Scheme 4

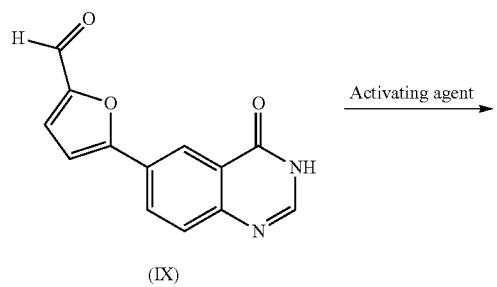

(IX)

Activating agent

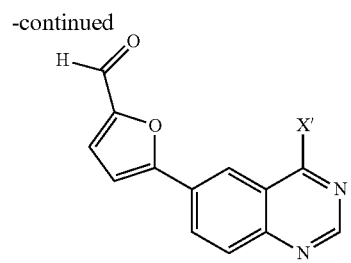

(X) (activated (IX))

X' = Cl, Br, I, OSO₂R, OPOCl₂, 6-benzotriazol-1-yloxy, [OP(NR₂)₃]BF₄ or PF₆

Preferably, the halogenating reagent is a chlorinating agent, such that X'=Cl.

Preferably, the chlorinating agent is SOCl₂, POCl₃, (COC)₂, PCl₃, PCl₅, COCl₂ or the like, and most preferably SOCl₂ or POCl₃. When these chlorinating agents are used, it is preferred that an amide such as DMF or DMAC, preferably DMF, is added in catalytic amounts. When these chlorinating agents are used, it is preferred that the hydrochloride salt of the compound of formula (Xa) ((Xa).HCl) is obtained.

Preferably, the sulfonating reagent is MsCl, p-TsCl, Tf₂O or the like.

Preferably, the bromination reagent is POBr₃, PBr₃ or the like.

Because the compound of formula (X) or its salt, such as (Xa).HCl where X'=Cl, is sensitive to moisture and other nucleophiles (including alcohols), it is preferred that it is processed (such as its isolation from the reaction product mixture) under conditions where it is not exposed to moisture. Following the preparation of the compound of formula (X) or (X).HCl it is directly isolated from the reaction product mixture by filtration or centrifugation and washed with a dry organic solvent, preferably dry MeCN (the Karl Fischer titration (KF) value is preferably no more than 100 ppm). The isolated compound of formula (X) or (X).HCl can be dried under vacuum with or without heating, but preferably the isolated compound of formula (X) or (X).HCl is directly used in the next reaction step, and it can still be used as a cake that is still moist from the washing solvent (e.g., MeCN).

The solvent in step ii) can be THF, MeCN, DMF, DMAC, 1,3-dimethyl-2-imidazolidinone (DMI), N-methylprrolidone (NMP), tetramethylurea (TMU), THF or MeCN and is preferably selected from dry (the KF value is preferably no more than 100 ppm) THF, DMF, MeCN, most preferably MeCN (the KF value is preferably no more than 100 ppm).

The addition of a base in step ii) is optional and less preferred. The base can be selected from imidazole, DIPEA, Et₃N and the like.

In one embodiment, (Xa).HCl reacts with the compound of formula (VII) in a solvent that does not substantially dissolve the hydrochloride salt of the compound of formula (IV) ((IV).HCl), preferably MeCN, without a base to give (IV).HCl. After the reaction completion, (IV).HCl is directly isolated by filtration. The isolated (IV).HCl is used in the step iii) with purification or without purification. Preferably, the isolated (IV).HCl is purified by being converted to its free base form, i.e., the compound of formula (IV), by the action of a base, preferably aqueous NaOH, in an organic solvent, preferably THF, and the free base of the compound of formula (IV) contained in the separated organic phase is converted into a salt by reaction with an acid. The acid can be aqueous HCl, HBr, p-TsOH, preferably HCl or p-TsOH. The new salt of the compound of formula (IV) can be isolated by filtration with very high purity and high potency assay.

In another embodiment, (Xa).HCl is reacted with the compound of formula (VII) in a polar solvent such as DMF, DMAC, DMI, NMP or TMU to give a homogeneous reaction solution. After the reaction is complete, water is added to precipitate the (IV).HCl. The (IV).HCl is then isolated by filtration.

In step iii), the salt of the compound of formula(IV) is reductively aminated with the commercially available hydrochloride salt of the compound of formula (VIII) ((VIII).HCl), a base, a carboxylic acid, a hydroxy containing compound and a reducing agent to provide lapatinib. Preferably the former reagents are mixture for a period of time, before the reducing agent is added. Preferably a water miscible solvent is used, most preferably THF. An organic base, preferably DIPEA, can be used. A carboxylic acid, preferably acetic acid, can be added to promote the reaction. The inventors discovered that when (VIII).HCl is used instead of the free base (VIII), a hydroxy containing compound, most preferably water in preferably 4.0 molar equivalents to 10.0 molar equivalents, can be added to assist the dissolution of (VIII).HCl. By contrast, the inventors discovered that when a water immiscible solvent, such as a dry water immiscible solvent, was used or when water was not present in the amination reaction, such as when a pre-dried solvent was used, the reaction proceeded more slowly and the compound of formula (IV) was not consumed effectively. Furthermore, if the compound of formula (IV) was not consumed effectively by the time at which the reducing agent was added, the newly formed lapatinib was then able to react with the unreacted compound of formula (IV) which lead to the formation of an undesired impurity. By adding water, however, the formation of the impurity was observed to be suppressed. This was an important discovery by the inventors because the crude lapatinib could be prepared in a more pure form. When water was added, 4.0 molar equivalents to 10.0 molar equivalents of water were preferably used and a preferably 1.3 molar equivalents to 2.0 molar equivalent excess, most preferably 1.3 molar equivalents to 1.6 molar equivalent of (VIII).HCl was used. In this way the impurity could be reduced to below 5 area % purity by HPLC. The reducing agent was preferably $NaBH(OAc)_3$.

Lapatinib prepared using the method of this embodiment can be isolated, or more preferably it can be directly converted into highly pure lapatinib ditosylate salt without isolation of the lapatinib from the step iii) reaction product mixture. The isolated lapatinib ditosylate has a HPLC purity of 97.0-99.9%, preferably >99.0%, most preferably >99.8%. The reaction product mixture from the step iii) is quenched with a basic aqueous solution such as aq. NaOH, separated and the organic phase is washed with an acidic aqueous solution such as aq. $NH_4Cl$. The organic phase is then filtered and lapatinib ditosylate as crystalline Form I is obtained by crystallisation from the organic phase in the presence of p-toluenesulfonic acid. The lapatinib ditosylate is isolated by filtration or centrifugation, or other methods of solid isolation.

Lapatinib ditosylate prepared by the embodiment of this invention can be recrystallised to provide crystalline Form 1 (U.S. Pat. No. 7,157,466 B2) and Form 2 (as disclosed in WO 2009/079541 A1).

Figure 10:
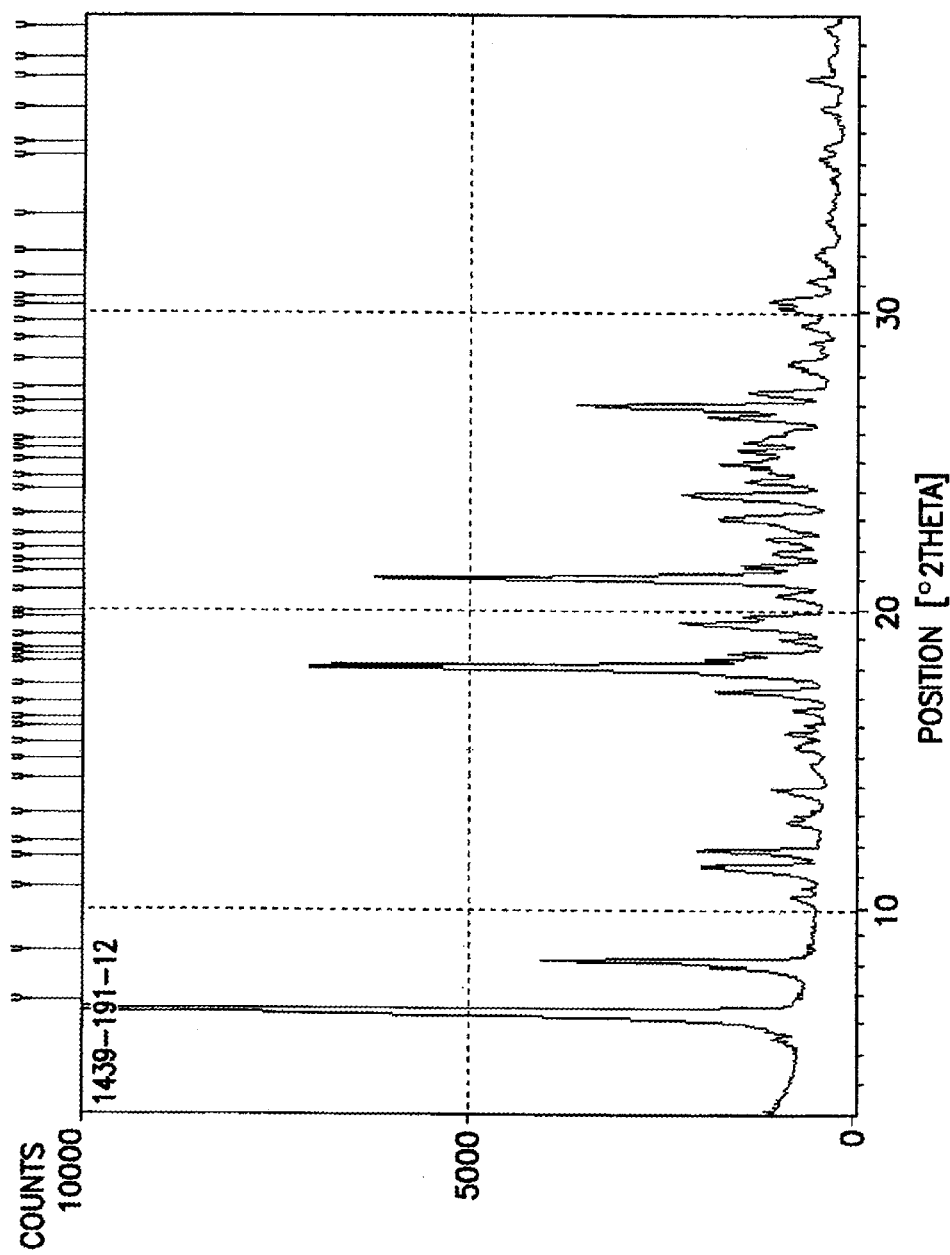
FIG. 10 shows the XRPD pattern of lapatinib ditosylate monohydrate prepared by a novel crystallisation process.

In another aspect of the present invention, lapatinib ditosylate monohydrate (as disclosed in U.S. Pat. No. 7,157,466 B2) is prepared by a novel method of crystallizing amorphous, crystalline Form I or crystalline Form II of lapatinib ditosylate from a solution composed from a mixture of DMSO, MeCN and water. XRPD analysis of this crystalline material provides an XRPD pattern as shown in FIG. 10. The prior art method for preparing lapatinib ditosylate monohydrate includes crystallisation from THF and water. This method can present some operation issues. Because lapatinib ditosylate Form I has a low solubility in THF and in water, which are the prior art crystallisation solvents, the THF and water must be pre-mixed and heated before dissolution of the solid. Because lapatinib ditosylate monohydrate has lower solubility in a THF and water mixture than does lapatinib ditosylate Form I, following the dissolution of the crude lapatinib ditosylate Form I, some lapatinib ditosylate monohydrate, which due to its lower solubility relative to Form I, can start to crystallise out. This provides operation issues when this crystallisation occurs during the polish filtration step and leads to loss of product yield and can cause filter blockage. The invention herein provides a novel process for the crystallization of amorphous, crystalline Form I or crystalline Form II of lapatinib ditosylate that alleviates the potential for this problem. In this novel process, lapatinib ditosylate is first fully dissolved in DMSO to provide a solution that can be polish filtered without any undesired, premature crystallisation of the monohydrate form occurring. Then following the polish filtration, aqueous MeCN is added, and the solution is slowly cooled which then allows the lapatinib ditosylate monohydrate to be crystallised in a controlled manner. This novel crystallisation process is advantageous on industrial production scales because it allows excellent control of when the crystallisation occurs.

In another embodiment, lapatinib is produced by:

i) Reacting the compound of formula (IX) with 2-(methylsulfonyl)ethanamine ((VIII)) or its salt (i.e., (VIII).HCl) to produce the compound of formula (XI);

ii) Activating the compound of formula (XI) with an activating agent to produce the compound of formula (XII); and iii) Converting the compound of formula (XII) into lapatinib by reaction of the compound of formula (XII) with the compound of formula (VII).

In step i), the compound of formula (IX) can be reductively aminated with (VIII).HCl and a reducing agent in a solvent, in the presence of a base, such as DIPEA, and in the presence of AcOH. The reducing agent is preferably $NaBH(OAc)_3$.

In step ii), the compound of formula (XI) is activated to allow its facile reaction with the compound of formula (VII) in step iii). In this way the compound of formula (XI) is converted to the compound of formula (XII) (Scheme 5) where X' is a leaving group that can be displaced upon reaction with the compound of formula (VII). For example, X'=Cl, Br, I, $OSO_2R$, $OPOCl_2$, 6-benzotriazol-1-yloxy, $[OP(NR_2)_3]BF_4$ or $PF_6$ with a halogenating, sulfonating, phosphonylating or amide bond-forming reagent; wherein R is alkyl, aryl, heteroaryl; and wherein $NR_2$ is a dialkylamine or a heterocyclic ring including the N within the ring. When R is alkyl, it can be acyclic or it can be cyclic such that $R_2$ together forms a ring (such as a 5 or 6 membered ring). Preferably, the activating agent is a halogenating reagent. Preferably the halogenating is a chlorinating agent, such that X'=Cl. Preferably, the chlorinating agent is $SOCl_2$, $POCl_3$, $(COCl)_2$, $PCl_3$, $PCl_5$, $COCl_2$ or the like, and most preferably $SOCl_2$ or $POCl_3$. When these chlorinating agents are used, it is preferred that an amide such as DMF or DMAC, preferably DMF, is added in catalytic amounts.

Scheme 5

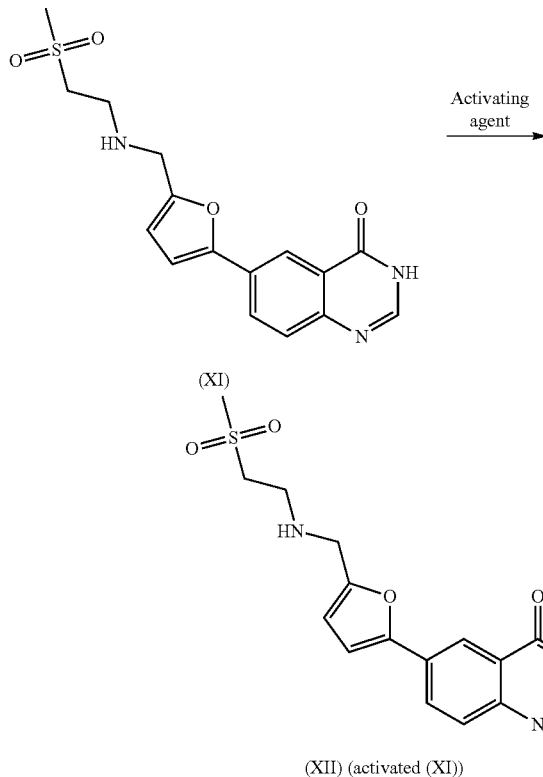

In step iii), the compound of formula (XII) is converted into lapatinib by reaction with the compound of formula (VII) in an organic solvent, optionally in the presence of a base. The solvent in step iii can be selected from THF, MeCN, i-PrOH, MEK, DMF, DMAC, 1,3-dimethyl-2-imidazolidinone (DMI), N-methylprrolidone (NMP) and tetramethylurea (TMU). The addition of a base in step iii) is optional, and the base can be selected from imidazole, DIPEA, Et$_3$N or the like.

Lapatinib prepared in this way can be isolated by crystallisation, as described above, or chromatography (such as flash chromatography or preparative HPLC), or it can be converted into lapatinib ditosylate.

In another embodiment, the novel compound of formula (IX) is prepared by reacting a compound of formula (V):

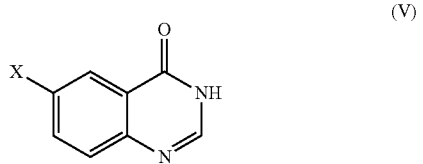

wherein X is a halogen, preferably I;
with a compound of formula (VI):

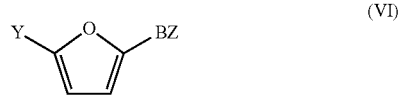

wherein
BZ is B(OH)$_2$, B(OR)$_2$, [BF$_3$]M, BR$_2$ or the like;
Y is CH=O, CH(OR)$_2$ or the like;
CH(OR)$_2$ and B(OR)$_2$ are cyclic or acyclic;
B(OR)$_2$ can be a boronic anhydride (i.e., also known as a boroxine or cyclotrimeric anhydride of a boronic acid).
R is alkyl, aryl, heteroaryl, allyl or the like;
M is a metal ion such as an alkaline metal, including potassium;
in the presence of an effective amount of catalyst, a base and a solvent.

Preferably the solvent is composed of an organic solvent and water.

Preferably, the compound of formula (VI) is of formula (VIa)

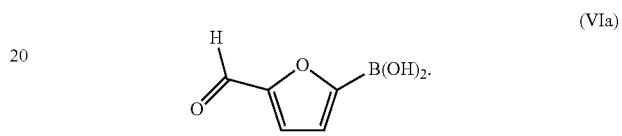

Preferably, the catalyst is composed from a ligand and a transition metal or transition metal salt. The catalyst can be prepared separately, before the coupling reaction, from a ligand and a transition metal, or it can be prepared in situ in the coupling reaction mixture by the addition of the ligand and a transition metal separately. Preferably the catalyst is prepared in situ in the coupling reaction mixture.

Preferably, the transition metal or transition metal salt is palladium or a palladium salt. Most preferably the transition metal salt is a palladium salt. When the transition metal is palladium, Pd(OAc)$_2$, Pd$_2$(dba)$_3$, Pd(PPh$_3$)$_4$, Pd[P(t-Bu)$_3$]$_2$ and the like can be used. Preferably Pd(OAc)$_2$ is used as the source of palladium metal for the catalyst.

Preferably, when the transition metal is palladium, the ligand is a phosphine selected from those reported in the literature for use in the Suzuki-Miyaura coupling reaction, including P(n-Bu)$_3$, P(t-Bu)$_3$, PCy$_3$, P(o-Tol)$_3$, dppe, dppp, dppb, dppf, Ph$_3$P, BINAP, BippyPhos, TrippyPhos. Preferably the phosphine ligand is P(t-Bu)$_3$ or its salt derivative. More preferably, the phosphine ligand is provided as the stable salt [HP(t-Bu)$_3$]BF$_4$. Although a range of phosphine ligands can be used in this coupling reaction the inventors observed that dppb, dppf, Ph$_3$P, BINAP, BippyPhos, TrippyPhos all provided inefficient couplings when combined to make catalysts with palladium metal or palladium metal salts. Given this the inventors were surprised when they discovered that P(t-Bu)$_3$, when was combined with Pd(OAc)$_2$, provided a catalyst that promoted a relatively efficient coupling of the compound of formulae (Va) and (VIa), as characterized by a good HPLC determined conversion (typically >=90%) of the compound of formula (Va) to the compound of formula (IX) when the bases Na$_2$CO$_3$ or KOAc were used, in a range of solvents such as aqueous dioxane, aqueous DMAC, aqueous DMF, aqueous NMP, aqueous MeCN, aqueous DMSO (see Table 1). The inventors found that it was preferred to handle P(t-Bu)$_3$ as its tetrafluoroborate salt, [HP(t-Bu)$_3$]BF$_4$, because this is an air stable and non-flammable solid.

Although the molar ratio between the palladium metal and the phosphine ligand can be varied, the inventors discovered that an about 1:1 molar ratio was preferred for a catalyst prepared from P(t-Bu)$_3$ and Pd(OAc)$_2$. Using a molar excess of P(t-Bu)$_3$ with respect to Pd(OAc)$_2$ did provide a benefit in terms of coupling efficiency of the compounds of formulae (Va) and (VIa).

The inventors discovered that when the catalyst is prepared in situ from [HP(t-Bu)$_3$]BF$_4$ and Pd(OAc)$_2$ that it could be used at low loadings. Preferably the catalyst is used at between 0.5 mol % and 5 mol %, preferably between 0.5 mol % and 2 mol %, with respect to the moles of the compound of formulae (Va).

Different bases can be used including inorganic or organic bases, such as those reported in the literature for use in the Suzuki-Miyaura coupling reaction. Preferably, the base is a hydroxide such as an alkali metal hydroxide, an alkaline earth metal hydroxide (such as Ba(OH)$_2$) or an ammonium hydroxide (such as Et$_4$NOH), an alkoxide such as an alkali metal alkoxide (such as NaOMe or NaOEt) or an ammonium alkoxide, or a metal carbonate such as an alkali metal carbonate (such as Na$_2$CO$_3$, K$_2$CO$_3$ and Cs$_2$CO$_3$) or an alkaline earth metal carbonate, metal bicarbonate such as an alkali metal bicarbonate (such as NaHCO$_3$ or KHCO$_3$) or an alkaline earth metal bicarbonate, an amine (such as triethylamine or DIPEA), or a metal carboxylate such an alkali metal carboxylate (such as potassium acetate), or a metal phosphate such as an alkali metal phosphate (such as K$_3$PO$_4$). Most preferably the base is potassium acetate (AcOK). The inventors discovered that the amount of base can be varied with respect to the other reactants, but it is preferred that when the base is Na$_2$CO$_3$ that between 0.8 to 2.5 molar equivalents with respect to the compound of formula (VI), and more preferably 1.0 to 1.5 molar equivalents with respect to the compound of formula (VI) are used. When the base is AcOK, it is preferred that not less than 1.0 molar equivalents with respect to the compound of formula (VI), and more preferably 1.0 molar equivalent with respect to the compound of formula (VI) is used.

It was discovered that mixtures of water miscible organic solvents and water was preferred as the reaction solvent. Mixtures of water with N,N-dimethylformamide (DMF), N,N-dimethylacetamide (DMAC), dimethyl sulfoxide (DMSO), N-methylprrolidone (NMP), acetonitrile (MeCN), dioxane or 2-methyl furan could be used. Other solvents including aromatic solvents or alcohol solvents with water, and also those reported in the literature for use in the Suzuki-Miyaura coupling reaction, might also be useful.

Preferably, the solvent is a mixture of water and DMSO. As well as providing a good solvent mixture for the efficient conversion of the compound of formulae (V) and (VI) to the compound of formula (IX), DMSO has a relatively low toxicity compared to some other solvents that can be used such as MeCN, DMF and dioxane. Moreover, using our preferred process conditions and operations, the compound of formula (IX) could be crystallised from the reaction product mixture when DMSO and water was used as the solvent.

It was discovered that when a water miscible organic solvent, such as DMSO, and water was used in the reaction that the volumetric ratio of the two solvents components was important. It was discovered by the inventors that it was most preferable when the reaction of the compound of formulae (Va) and (VIa) was conducted in a homogeneous solution. This enabled efficient reaction with good conversion of the starting materials to the product, and allowed the product of formula (IX) to be isolated with a relatively low residual palladium level. When the reaction was conducted under homogeneous conditions the residual palladium concentration in the compound of formula (IX) was <300 ppm, but when the reaction was conducted under heterogeneous conditions the residual palladium concentration in the compound of formula (IX) was >500 ppm. For example, when a 2:1 mixture (30 volumes) of DMSO and H$_2$O was used, the reaction was heterogeneous, and the compound of formula (IX) produced contained a residual palladium concentration of 536 ppm. In this case, because the reaction was heterogeneous the compound of formula (IX) was isolated without hot-filtration and without crystallisation. Thus, by contrast it is advantageous to use a solvent system that provides a homogeneous reaction solution during the coupling reaction. A range of volumetric ratios of the two solvents components can be utilised to obtain a homogeneous solution at the preferred reaction temperature, but this is solvent dependent. When DMSO is used as the solvent with the compound of formulae (Va) and (VIa) within the preferred reaction temperature range, the volumetric ratios of DMSO to water is preferable between 5:1 to 2:1, mostly preferably about 5:2.

The reaction can be conducted at about 70° C. to 100° C., but at internal temperature of about 75° C. to 85° C. is preferred when the solvent is DMSO and water with a volumetric ratio about 5:2 when the compound of formulae (Va) and (VIa) were used.

When the coupling reaction is complete, as can be determined by HPLC analysis of the reaction solution, the reaction product mixture is optionally, but preferably, filtered whilst still hot and whilst the compound of formula (IX) is still dissolved in the solvent mixture, such as at about 70° C. to 100° C. when the solvent is composed of about 5:2 DMSO to water. Without being bound by theory, it is believe that the hot filtration functions to remove some of the palladium that precipitates from the reaction product mixture during the reaction, thereby reducing the residual palladium level in the product of formula (IX). Therefore a hot filtration step is advantageous. Optionally, more hot water can be added to the homogenous solution of the compound of formula (IX), following the hot filtration step and the solution is allowed to cool resulting in precipitation of the compound of formula (IX). The compound of formula (IX) is then isolated by filtration or centrifugation or other methods of isolating solids.

Figure 2:
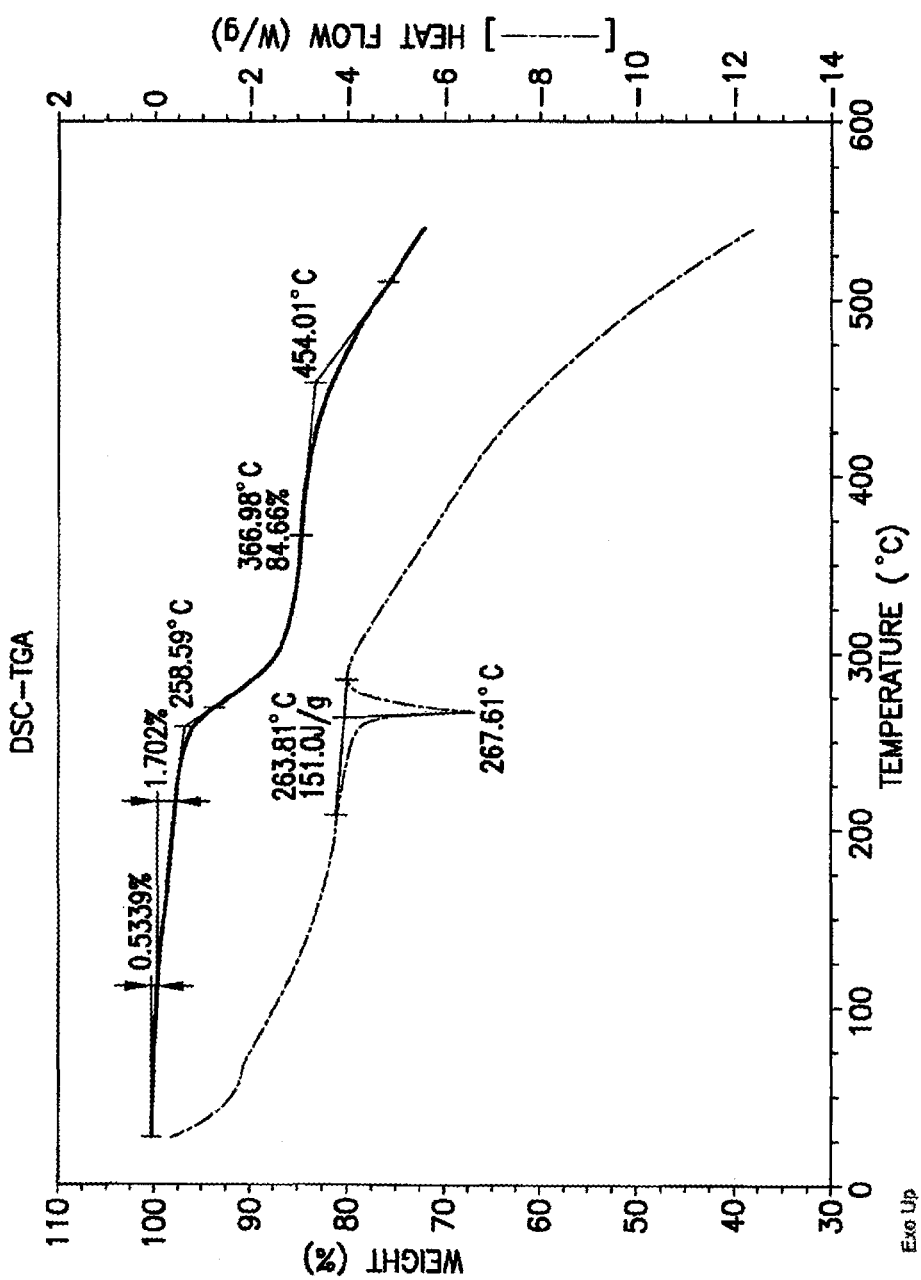
FIG. 2 shows the DSC/TGA trace of the compound of formula (IX).
Figure 3:
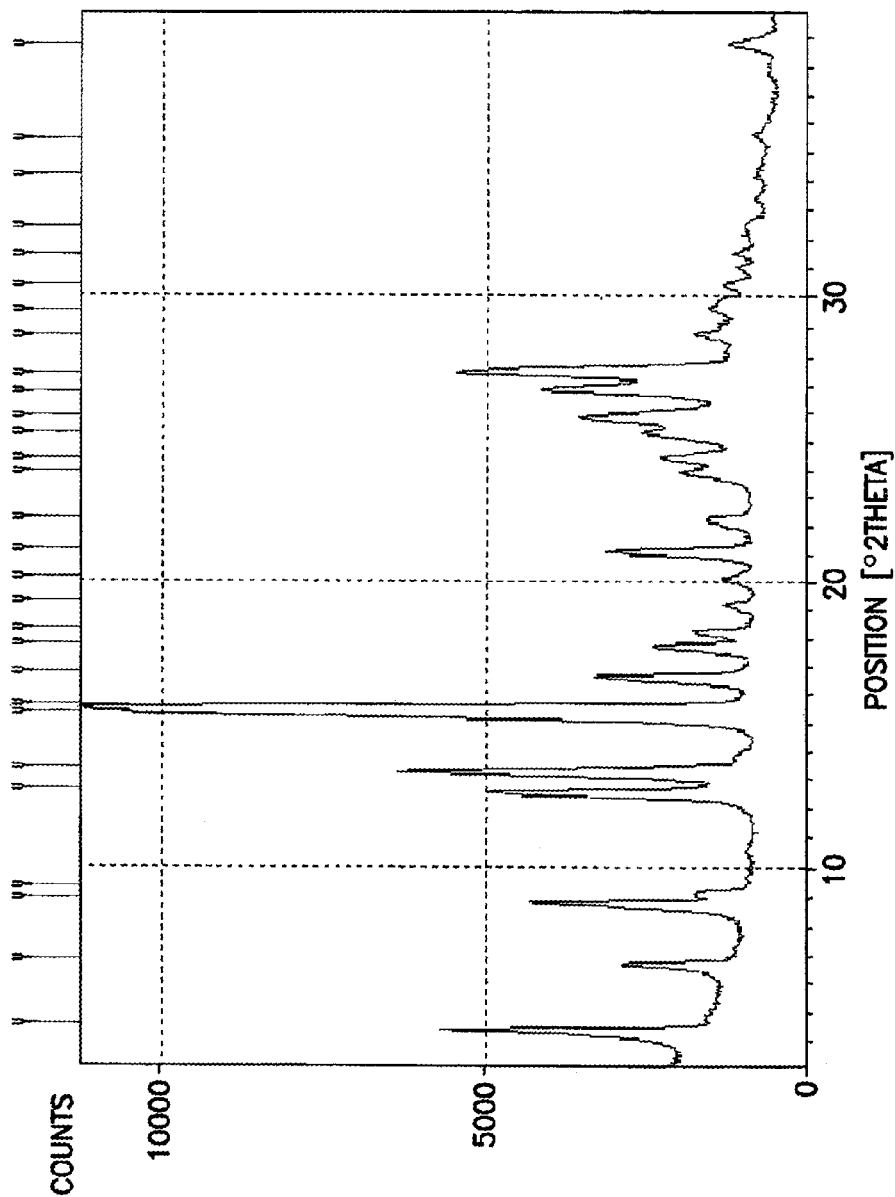
FIG. 3 shows the X-ray powder diffraction (XRPD) pattern of the compound of formula (IX).
Figure 4:
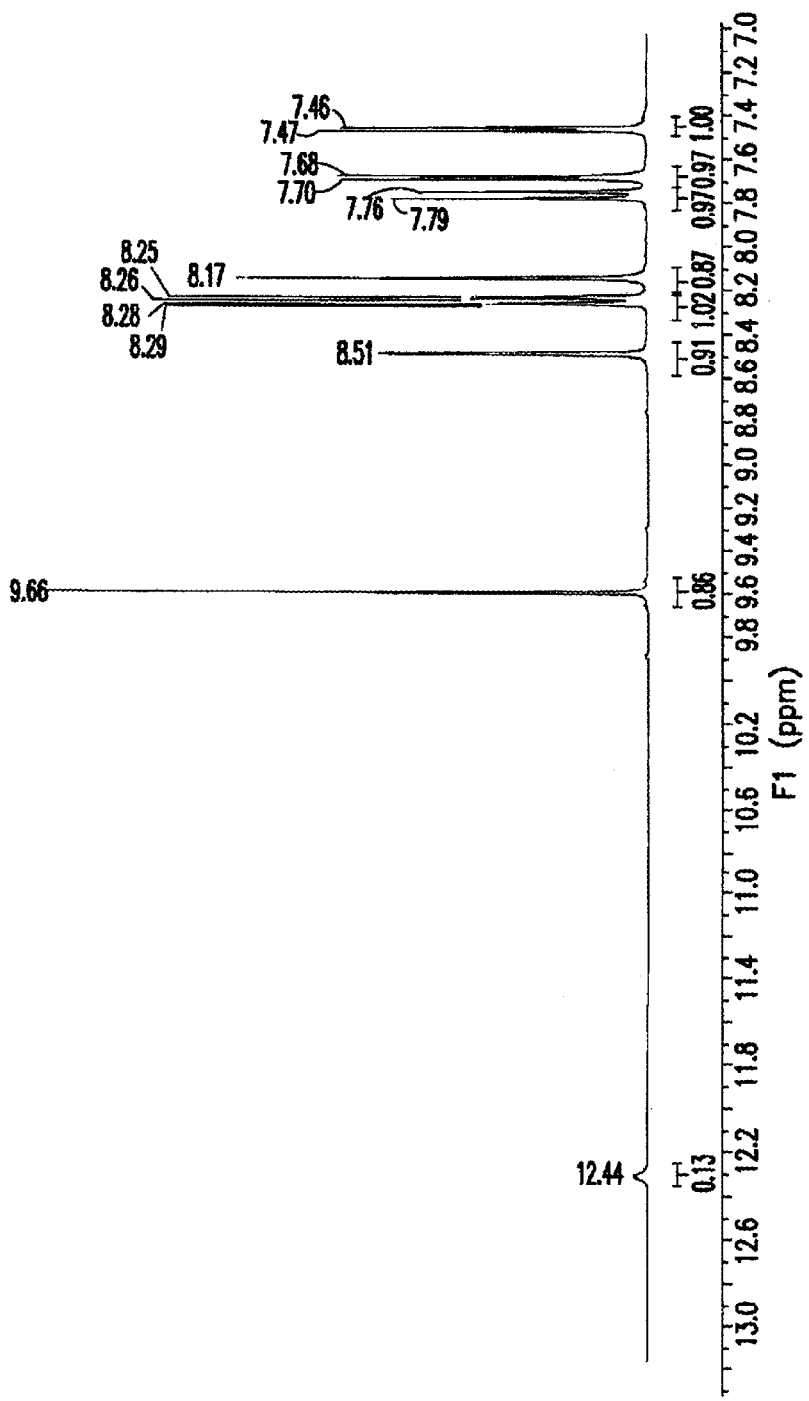
FIG. 4 shows the $^1$H NMR spectrum of the compound of formula (IX).
Figure 5:
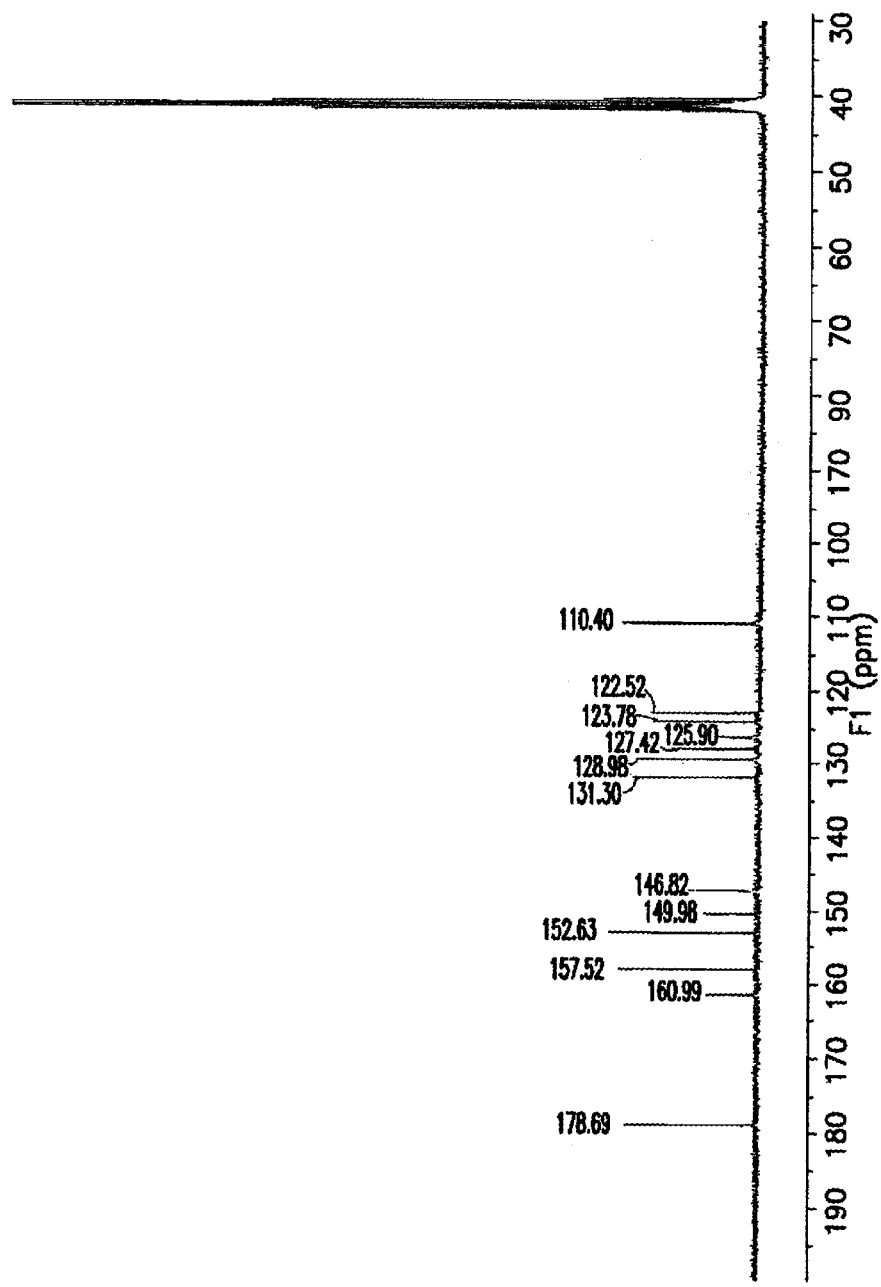
FIG. 5 shows the $^{13}$C NMR spectrum of the compound of formula (IX).
Figure 6:
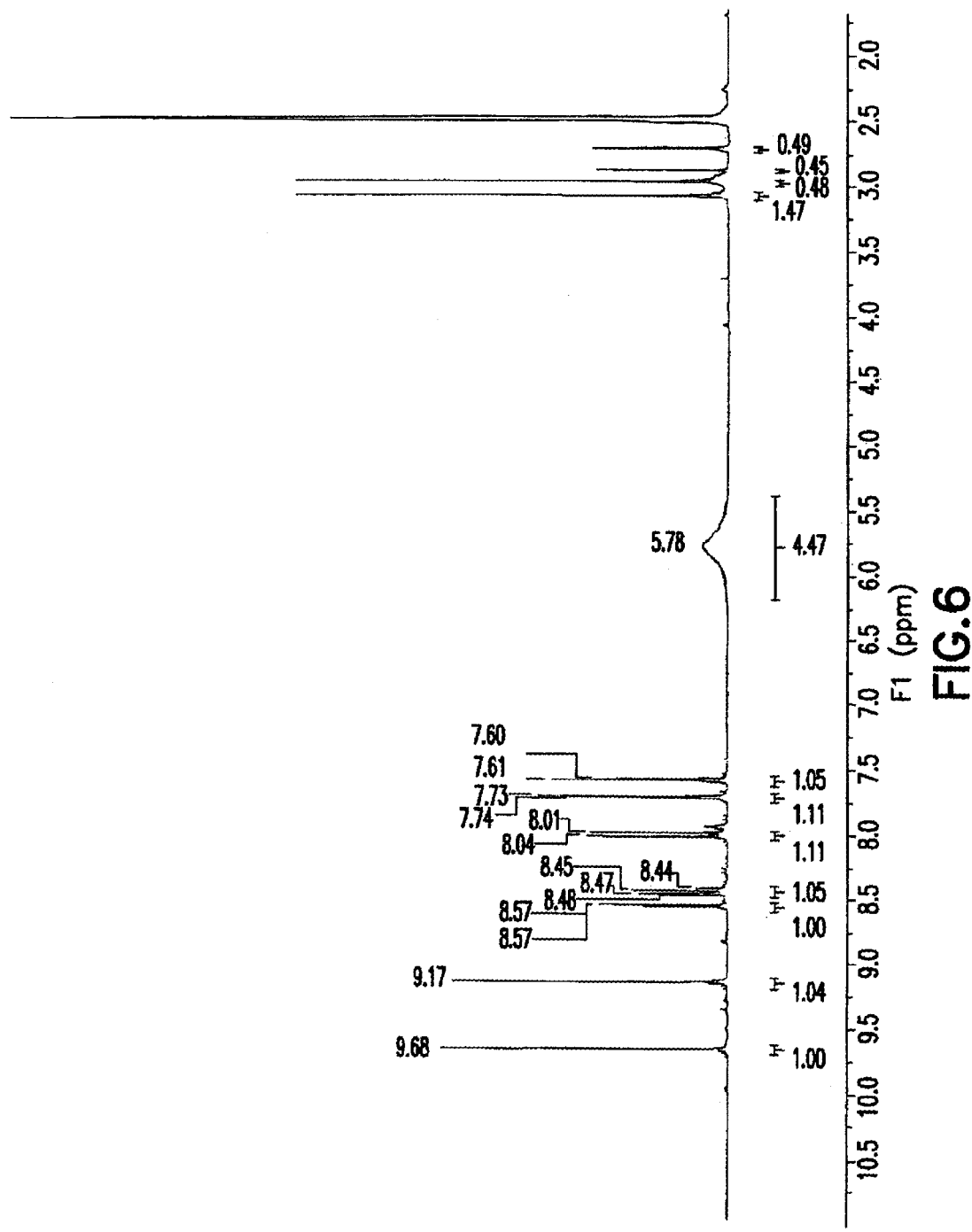
FIG. 6 shows the $^1$H NMR spectrum of (Xa).HCl.
Figure 7:
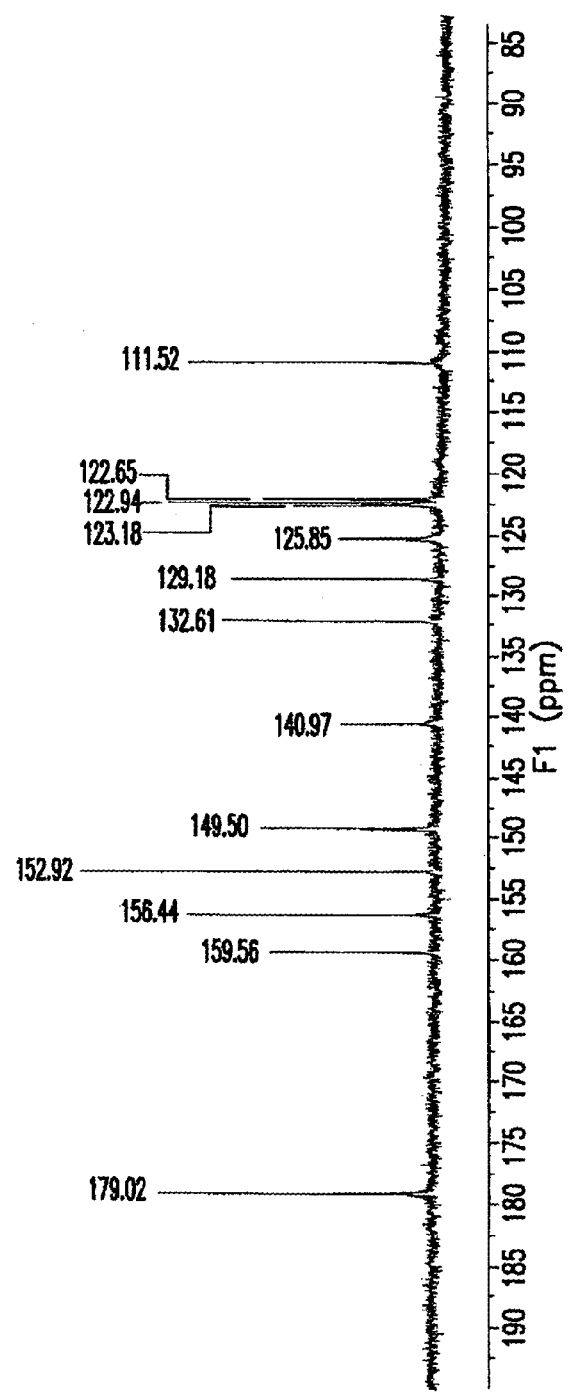
FIG. 7 shows the $^{13}$C NMR spectrum of (Xa).HCl.
Figure 8:
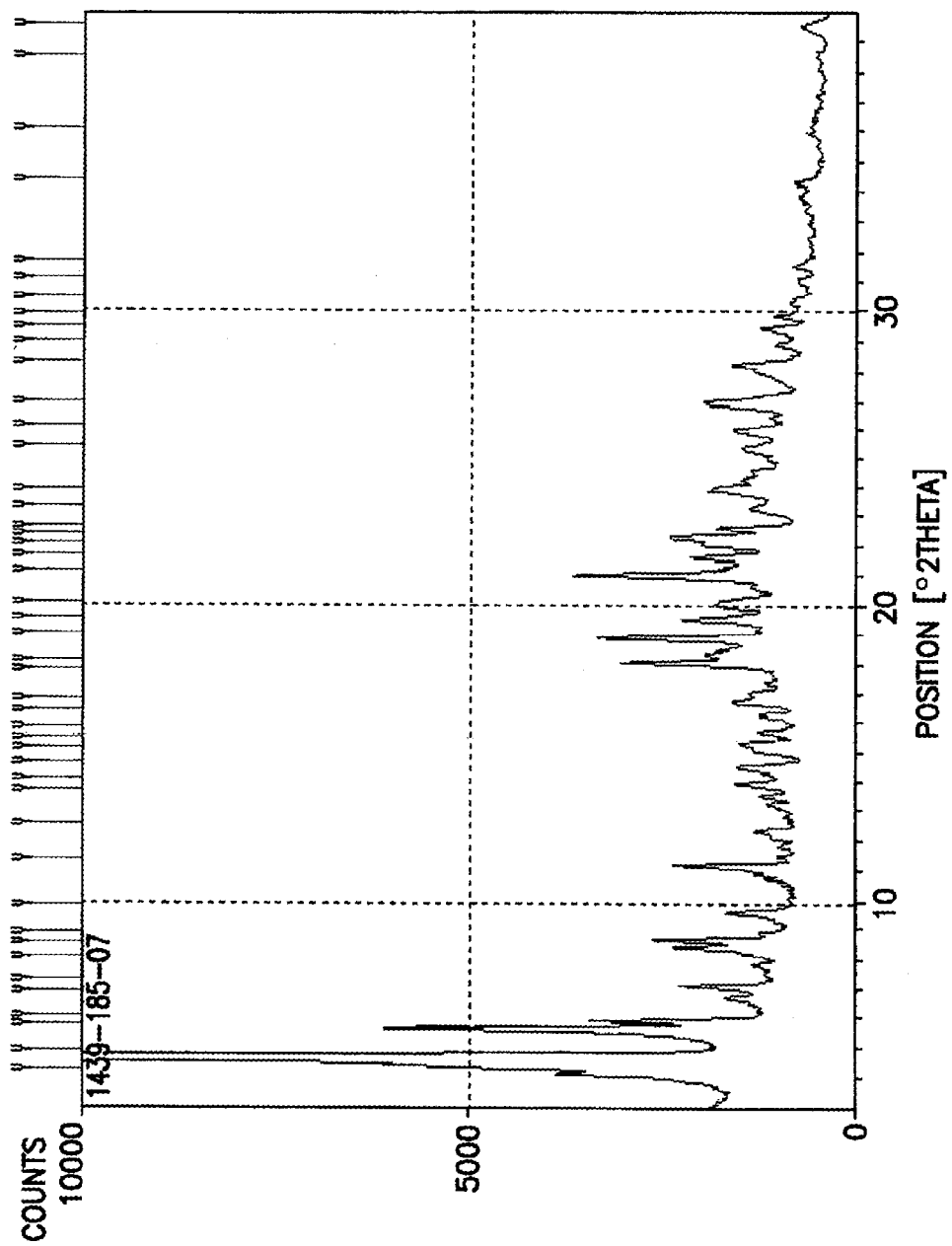
FIG. 8 shows the XRPD pattern of lapatinib ditosylate Form 1 (Form 1 is disclosed in U.S. Pat. No. 7,157,466 B2).

The compound of formula (IX) prepared in this manner is of high quality as judged by HPLC analysis, and $^1$H and $^{13}$C NMR spectroscopy (see FIG. 4 and FIG. 5). HPLC analysis of the compound of formula (IX) prepared using the method of this invention was of >98% HPLC purity based on area %, and was typically >=99.0% HPLC purity. The reaction was efficient and yields of >90% were typically achieved, often the yields were between 92-95%. When the compound of formula (IX) was precipitated from the product mixture with addition water added, with cooling, the compound of formula (IX) was found to be crystalline. A crystalline form of the compound of formula (IX) as one embodiment of the invention is characterized by its XRPD pattern (FIG. 3), DSC trace (FIG. 2) and IR spectrum (FIG. 1). Although this crystalline form of the compound of formula (IX) is useful in the synthesis of the compound of formula (Xa), the invention is not restricted to this crystalline form's use and amorphous or other crystalline forms, such as polymorphs or solvates could be applied in the synthesis of the compound of formula (Xa) from the compound of formula (IX).

The compound of formula (IX) prepared using this embodiment of the invention can be used to prepare lapatinib and lapatinib ditosylate of high quality with an acceptable concentration of residual palladium.

EXAMPLES

Example 1

Synthesis of 5-(4-oxo-3,4-dihydroquinazolin-6-yl) furan-2-carbaldehyde (IX)

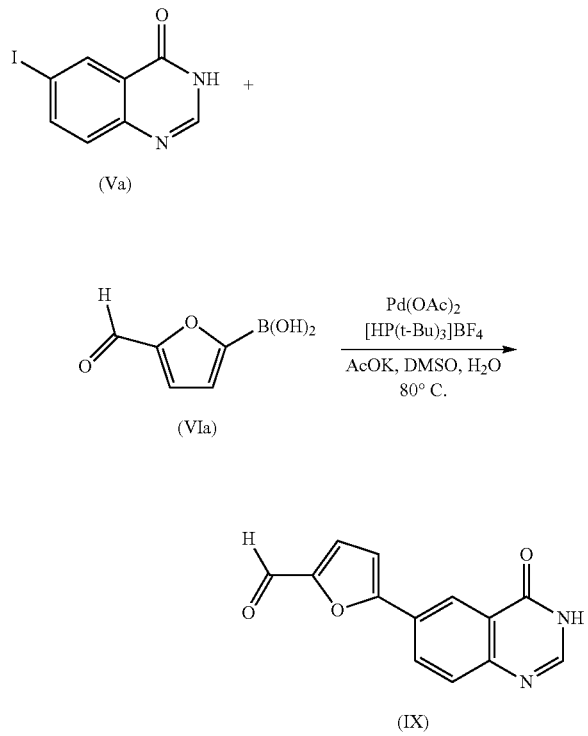

A 5:2 v/v mixture of DMSO and H₂O (1400 mL) was degassed for 30 min at ambient temperature using nitrogen. 5-Formylfuran-2-ylboronic acid ((VIa); 26.8 g, 193 mmol) was added dissolved in this mixture. [HP(t-Bu)₃]BF4 (840 mg, 2.94 mmol) and Pd(OAc)₂ (680 mg, 2.94 mmol) was added and the mixture was stirred at ambient temperature under an atmosphere of nitrogen for 20 min AcOK (18.8 g, 192 mmol) was added into the reactor and was stirred for 20 min at ambient temperature. 6-Iodoquinazolin-4(3H)-one ((Va); 40 g, 147 mmol) was added and heated to 80±5° C. (internal temperature) in an oil bath under nitrogen. Upon completion of the reaction (HPLC), the reaction mixture was hot-filtered, then hot water (400 mL, 80±5° C.) was added into the filtrate. This was slowly cooled to 0-15° C. (solid started to precipitate at 70° C. (internal temperature) and was then filtered. The filter cake was washed with H₂O (80 mL), then with MeCN (60 mL), and dried in vacuo at 60±5° C. for 6 h to provide 5-(4-oxo-3,4-dihydroquinazolin-6-yl)-furan-2-carbaldehyde ((IX); 34.6 g, 144 mmol) with 99.7% HPLC purity in 97.6% HPLC yield. $^1$H NMR (300 MHz, d$_6$-DMSO): δ 7.47 (d, J=3.8 Hz, 1H), 7.69 (d, J=3.8 Hz, 1H), 7.77 (d, J=8.6 Hz, 1H), 8.17 (s, 1H), 8.27 (dd, J=8.6, 2.1 Hz, 1H), 8.52 (d, J=2.1 Hz, 1H), 9.66 (s, 1H); $^{13}$C NMR (75 MHz, CDCl₃): δ 110.5, 122.6, 123.9, 126.0, 127.5, 129.0, 131.4, 147.1, 150.1, 152.7, 157.6, 161.2, 178.8; ESI-MS, Pos: [M+H]⁺ m/z 241; IR (cm⁻¹): 1713, 1671, 1604,1462; m.p.: 267° C. See FIG. 2 for the DSC/TGA of the compound of formula (IX); See FIG. 3 for the X-ray powder diffraction pattern of the compound of formula (IX); Residual concentration of palladium: 230 ppm.

Example 2

Synthesis of 5-(4-chloroquinazolin-6-yl)furan-2-carbaldehyde hydrochloride ((Xa).HCl)

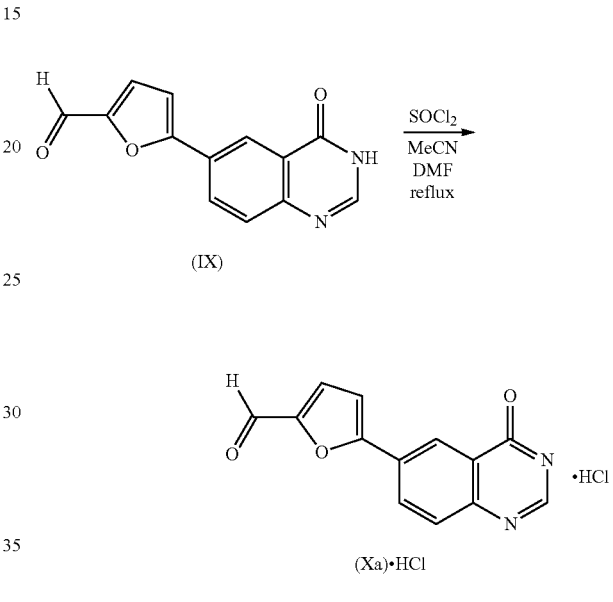

Over a 1.5 hour period under an atmosphere of N₂, SOCl₂ (86.2 g) in MeCN (145 mL) was added dropwise into a mixture, that had been preheated at reflux for 0.5 h, of the compound of formula (IX) (29 g, 0.121 mol), MeCN (435 mL) and DMF (0.88 g) at reflux. The reaction was terminated when less than 2% (HPLC) of the compound of formula (IX) was remaining. If the reaction did not achieve complete reaction, extra SOCl₂ was added. The mixture was cooled to about 25±5° C. (internal temperature), and was then filtered and washed with MeCN (58 mL) to give ca. 55 g of (Xa).HCl (moist with MeCN) with 82A % purity by HPLC. (Xa).HCl: $^1$H NMR (300 MHz, d₆-DMSO): δ 9.68 (s, 1H), 9.17 (s, 1H), 8.57 (d, J=2.0 Hz, 1H), 8.46 (dd, J=8.6, 2.1 Hz, 1H), 8.02 (d, J=8.6 Hz, 1H), 7.74 (d, J=3.8 Hz, 1H), 7.60 (d, J=3.8 Hz, 1H). See FIG. 5 for the $^1$H NMR spectrum of (Xa).HCl; $^{13}$C NMR (75 MHz, d₆-DMSO) δ 179.0, 159.6, 156.4, 152.9, 149.5, 141.0, 132.6, 129.2, 125.9, 123.2, 122.9, 122.7, 111.5.

(Xa).HCl was purified by column chromatography (eluting with EtOAc/DCM, 1:8) to give pure compound of formula (Xa). The compound of formula (Xa): $^1$H NMR (300 MHz, d₆-DMSO): δ 7.53 (d, J=3.3 Hz, 1H), 7.68 (d, J=3.3 Hz, 1H), 8.02 (d, J=8.7 Hz, 1H), 8.42 (d, J=8.4 Hz, 1H), 8.54 (d, J=2.1 Hz, 1H), 8.90 (s, 1H), 9.64 (s, 1H); $^{13}$C NMR (75 MHz, CDCl₃): δ 111.5, 122.8, 122.9, 123.7, 125.9, 129.1, 132.5, 142.1, 149.3, 152.9, 156.6, 159.7, 179.1.

Example 3

Synthesis of 5-(4-(3-chloro-4-(3-fluorobenzyloxy)phenylamino)-quinazolin-6-yl)furan-2-carbaldehyde hydrochloride ((IV).HCl)

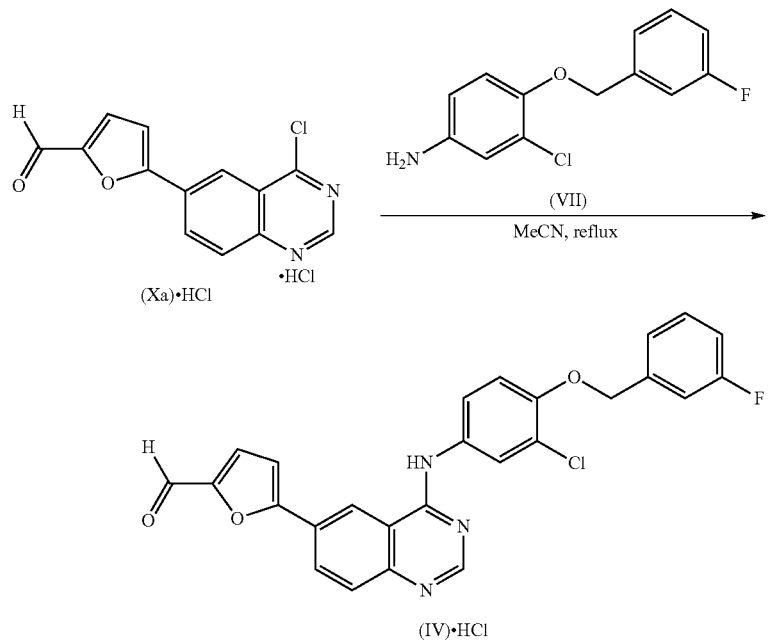

A mixture of (Xa).HCl (moist with MeCN solvent, prepared from 29 g of the compound of formula (IX), 0.120 mol) and 3-chloro-4-(3-fluorobenzyloxy)aniline ((VII); 27.3 g, 0.108 mol) in MeCN (580 mL) was stirred under reflux, until HPLC analysis showed that the reaction was completed (about 2 h). The mixture was cooled to room temperature (25±5° C.), filtered, and washed with MeCN (58 mL). A mixture of the moist crude solid of the compounds of formula (IV) and THF (870 mL) was treated with a 2.0 N aqueous NaOH (348 mL) and stirred for 3-4 h until most of the solid had dissolved. The mixture was filtered through diatomite and was washed with a saturated aqueous solution of NaCl (87 mL). The organic layer was treated with 10% aqueous HCl (174 mL) and stirred for 0.5 h. The resulting solid was filtered, washed with THF (87 mL), and dried in vacuo at 60±5° C. for 16 h to give the crude (IV).HCl (34 g, 0.067 mol, HPLC purity: 99%).

(IV).HCl: $^1$H NMR (300 MHz, d$_6$-DMSO): δ 9.69 (s, 1H), 9.52 (s, 1H), 8.94 (s, 1H), 8.50 (dd, J=8.8, 1.7 Hz, 1H), 8.01 (d, J=8.8 Hz, 1H), 7.97 (d, J=2.5 Hz, 1H), 7.77 (d, J=3.8 Hz, 1H), 7.73 (dd, J=9.0, 2.5 Hz, 1H), 7.69 (d, J=3.8 Hz, 1H), 7.49 (td, J=8.0, 6.1 Hz, 1H), 7.41-7.28 (m, 3H), 7.20 (td, J=8.4, 2.2 Hz, 1H), 5.31 (s, 2H).

Free base of the compound of formula (IV) is obtained by column chromatography (eluting with EtOAc/DCM, 1:4, v/v). The compound of formula (IV) $^1$H NMR (300 MHz, d$_6$-DMSO): δ 5.28 (s, 2H), 7.19 (td, J=8.7 Hz, J=2.1 Hz 1H), 7.34 (m, 4H), 7.43 (d, J=3.6 Hz, 1H), 7.49 (m, 1H), 7.73 (dd, J=8.7 Hz J=2.7 Hz, 1H), 7.76 (d, J=3.6 Hz, 1H), 7.88 (d, J=9 Hz, 1H), 8.07 (d, J=2.1 Hz, 1H), 8.32 (dd, J=4.43 Hz, J=1.95 Hz, 1H), 8.95 (d, J=1.5 Hz, 1H), 9.68 (s, 1H).

Example 4

Synthesis of N-(3-chloro-4-(3-fluorobenzyloxy)phenyl)-6-(5-((2-(methylsulfonyl)ethylamino)methyl)furan-2-yl)quinazolin-4-amine ditosylate (lapatinib ditosylate)

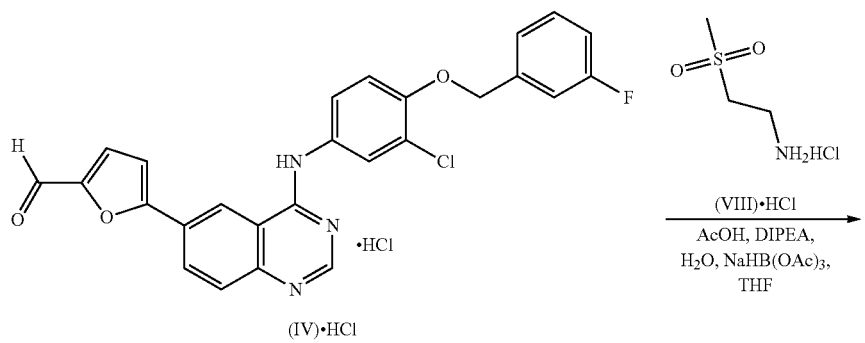

-continued

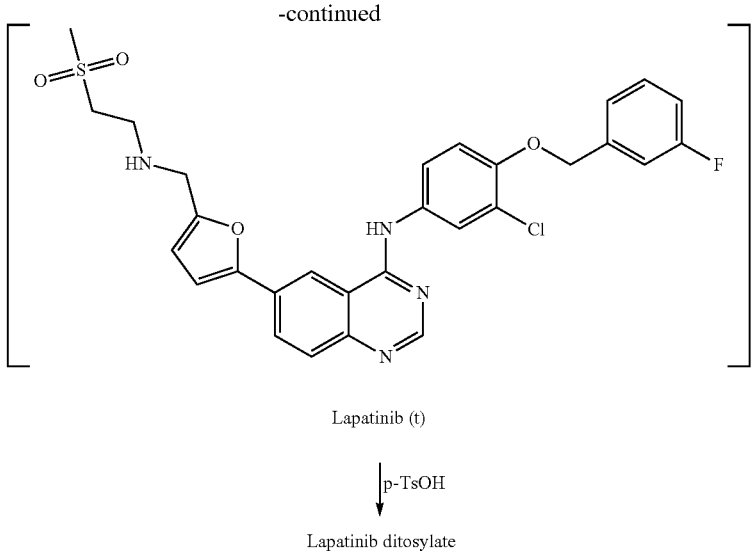

Lapatinib (t)

↓ p-TsOH

Lapatinib ditosylate

To a suspension of 2-(methylsulfonyl)ethanamine hydrochloride ((VIII).HCl; 12.2 g, 76.7 mmol) in THF (600 mL) was added acetic acid (14.1 g, 235 mmol) followed by DIPEA (30.3 g, 235 mmol) were added. After stirred at ambient temperature for 0.5 h, $H_2O$ (4.2 g, 233 mmol) and (IV).HCl (30.0 g, HPLC assay >99%, 58.7 mmol) were added. After being stirred at ambient temperature (20° C.) for 4 h, sodium triacetoxyborohydride (37.4 g, 176 mmol) was added and the mixture was stirred at ambient temperature (20° C.±5° C.; external temperature) until HPLC showed the completion of the reaction. A 10% aqueous solution of sodium hydroxide (90 mL) was added and the mixture was stirred for 30 min. The organic phase was washed with 25% aqueous $NH_4Cl$ (60 mL), filtered, treated with p-TsOH (40.4 g, 135 mmol) and heated to reflux for 2 h. The mixture was cooled to ambient temperature and stirred for 3 h at ambient temperature. The mixture was filtered, and the filter cake was washed twice with THF (120 mL each) and was then dried under vacuum at 70±5° C. for 6 h to give 43 g (46.5 mmol) lapatinib ditosylate with 99.4% HPLC purity.

Lapatinib ditosylate $^1H$ NMR (300 MHz, $d_6$-DMSO): δ 11.41 (s, 2H), 9.33 (s, 3H), 9.04 (d, J=1.3 Hz, 2H), 8.93 (s, 2H), 8.41 (dd, J=8.8, 1.6 Hz, 2H), 7.91 (d, J=2.6 Hz, 2H), 7.54-7.41 (m, 9H), 7.37-7.27 (m, 6H), 7.25 (d, J=3.4 Hz, 2H), 7.22-7.13 (m, 2H), 7.08 (dd, J=8.4, 0.6 Hz, 8H), 6.87 (d, J=3.5 Hz, 2H), 5.29 (s, 4H), 4.46 (s, 4H), 3.65-3.51 (m, 4H), 3.51-3.38 (m, 4H), 2.26 (s, 12H).

A solution of lapatinib ditosylate was converted to its free base form, lapatinib, by washing a solution with aqueous NaOH followed by concentration. Lapatinib: $^1H$ NMR (300 MHz, $d_6$-DMSO): δ 2.98 (t, J=6.75 Hz, 1H), 3.04 (s, 1H), 3.29 (t, J=6.6 Hz, 1H), 3.83 (s, 1H), 5.28 (s, 1H), 6.50 (d, J=3.0 Hz, 1H), 7.08 (d, J=3.3 Hz, 1H), 7.20 (m, 1H), 7.33 (m, 4H), 7.48 (m, 1H), 7.76 (m, 1H), 7.80 (d, J=9 Hz, 1H), 8.04 (d, J=2.75 Hz, 1H), 8.17 (dd, J=8.7 Hz, J=1.8 Hz, 1H), 8.56 (s, 1H), 8.75 (d, J=1.8 Hz, 1H).

Example 5a

Purification of Lapatinib Ditosylate

Lapatinib ditosylate (5.0 g, 5.4 mmol, 96.5% HPLC purity with the maximum individual impurity at 0.8%) was dissolved in DMSO (10 mL) at 70° C. (internal temperature). MeCN (10 mL) was added dropwise into the mixture at 70-80° C. (internal temperature) and was stirred at this temperature for 1 h. Over a 4 h period the mixture was cooled to room temperature. MeCN (30 mL) was added dropwise, and the mixture was stirred for 1 h, then filtered and washed with MeCN (10 mL). The filter cake was dried under vacuum at 60° C. for 16 h to give 4.0 g lapatinib ditosylate as crystalline Form 1 (as disclosed in U.S. Pat. No. 7,157,466 B2) with 99.6% HPLC purity in 78% HPLC yield.

Example 5b

Purification of Lapatinib Ditosylate

Figure 9:
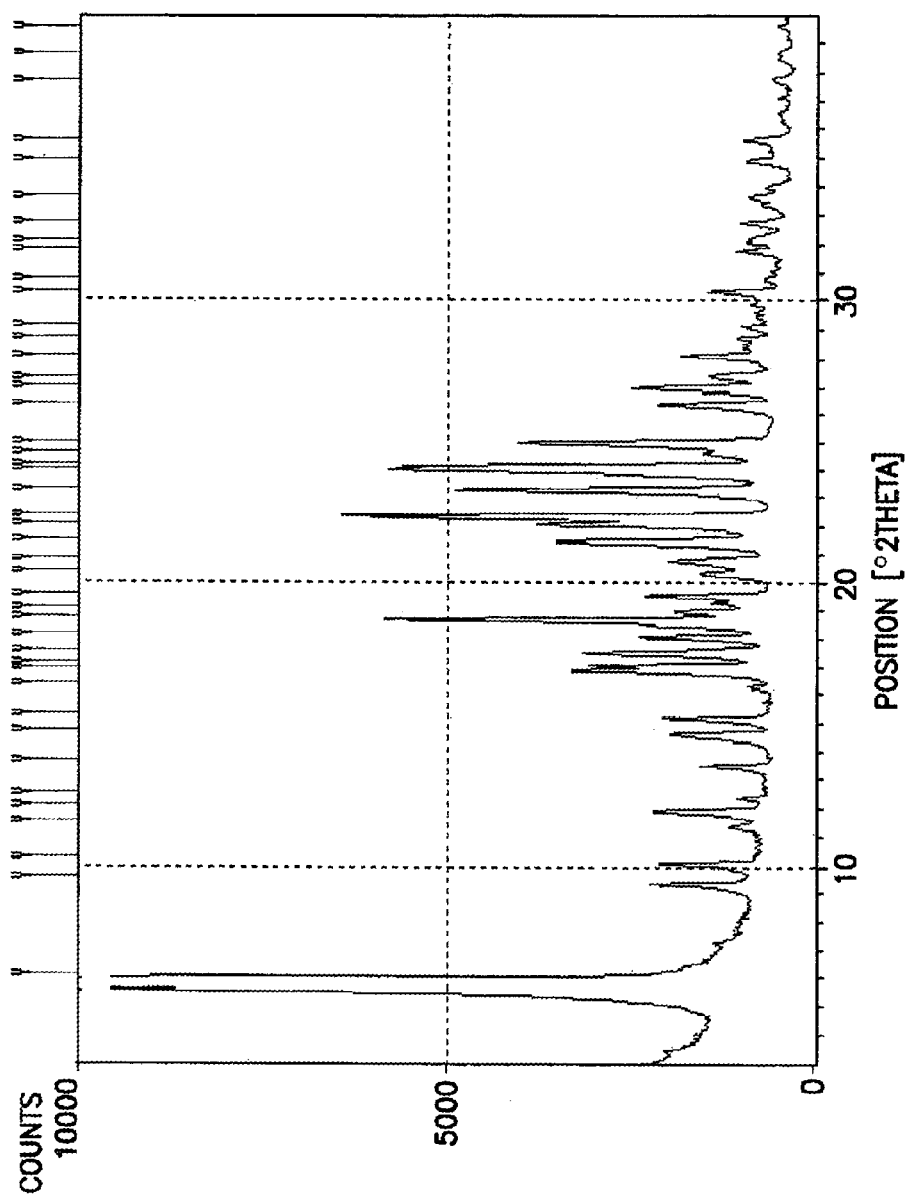
FIG. 9 shows the XRPD pattern of lapatinib ditosylate Form 2 (Form 2 is disclosed in WO 2009/079541 A1).

Lapatinib ditosylate (3 g, 3.25 mmol, 99.3% HPLC purity was dissolved in DMF (18 mL) at 80° C. and stirred for 1 hour. The mixture was hot-filtered. MeCN (18 mL) was added into the filtrate at 80° C. The temperature was cooled to 70° C. and crystal precipitated. The mixture was kept at 70° C. for 1 h and then 60° C. for 1 h. The mixture was further cooled to 0° C. and stirred for 2 h. The crystals of lapatinib ditosylate were isolated by filtration and were dried at 40° C. under vacuum overnight. Lapatinib ditosylate (2.5 g, 2.70 mmol, 83% yield) with 99.9% HPLC purity was obtained. XRPD analysis (FIG. 9) indicated that this was Form 2 as disclosed in WO 2009/079541 A1.

Example 6

Preparation of Lapatinib Ditosylate Monohydrate

Lapatinib ditosylate (2.0 g, 96.7% HPLC purity, 2.1 mmol) was dissolved in DMSO (5 mL) at 80° C. (internal temperature) and the solution was filtered whilst the lapatinib ditosylate was still dissolved. A mixture of MeCN (5 mL, 2.5 P) and water (0.3 mL) was then added dropwise into the filtered solution at 70-80° C. (internal temperature). The mixture was cooled at a rate of 10° C./h until 60° C., and was kept at 60° C. for 2 h and was then slowly cooled down to 50° C. After being kept at 50° C. for 1 h, MeCN (15 mL) was added, and then the mixture was cooled to 20-30° C. and stirred at 20-30° C. for 2 h. The slurry was filtered, washed with MeCN (6 mL) and the filter cake was dried in vacuo at 60° C. for 4 h to give lapatinib ditosylate monohydrate (1.7 g, 99.4A % purity, 1.8 mmol). XRPD analysis (FIG. 10) indicated that this was the monohydrate crystalline form as disclosed in U.S. Pat. No. 7,157,466 B2.

Example 7

Synthesis of 6-(5-((2-(methylsulfonyl)ethylamino)methyl)furan-2-yl)quinazolin-4(3H)-one ((XI))

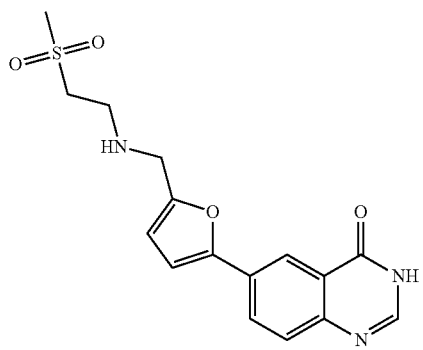

(XI)

To a suspension of the compound of formula (IX) (5 g, 21 mmol) and 2-(methylsulfonyl)ethanamine hydrochloride (4.1 g, 33 mmol) in THF (150 mL) was added acetic acid (5 g, 83 mmol) followed by DIPEA (10.5 g, 83 mmol). The mixture was stirred at 35° C. (internal temperature) for 2.5 h and was then cooled to 20° C. (internal temperature). Sodium tri-acetoxyborohydride (8.8 g, 42 mmol) was added and the mixture was stirred at ambient temperature the reaction was complete (TLC analysis). 25% Aqueous sodium hydroxide (10 mL) and water (50 mL) were added and the mixture was stirred for 30 min The liquid phases were separated and the aqueous layer was extracted with THF (50 mL). The extract was combined with the former organic layer and the mixture was washed with saturated aqueous $NH_4Cl$ (50 mL). The organic layer was concentrated under vacuum. The crude product was purified by column chromatography, eluting with 5% MeOH in DCM providing the compound of formula (XI) (3.1 g) after evaporation of the product containing fractions. The compound of formula (XI): $^1$H NMR (300 MHz, $d_6$-DMSO): δ 2.94 (dt, J=13.8 Hz, J=7.05 Hz, 1H), 3.00 (s, 1H), 3.24 (t, J=6.75 Hz, 1H), 3.77 (s, 1H), 6.42 (d, J=3.3 Hz, 1H), 7.03 (d, J=3.0 Hz, 1H), 7.68 (d, J=8.4 Hz, 1H), 8.06 (s, 1H), 8.09 (dd, J=8.55 Hz, J=2.25 Hz, 1H), 8.31 (d, J=2.1 Hz, 1H).

Example 8

Synthesis of Lapatinib from N-((5-(4-chloro quinazolin-6-yl)furan-2-yl)methyl)-2-(methylsulfonyl)ethanamine ((XIIa))

To a suspension of the compound of formula (XI) (0.4 g, 1.15 mmol) in toluene (10 mL) was added $POCl_3$ (0.21 g, 1.38 mmol) followed by $Et_3N$ (0.14 g, 1.38 mmol). After stirring at 90° C. for 2 h the mixture was cooled to ambient temperature and the compound of formula (VII) (0.6 g, 2.39 mmol) in MEK (20 mL) was added. The mixture was stirred at 90° C. for 2 h, cooled to ambient temperature, and 1 N aqueous sodium hydroxide (20 mL) and THF were added. The aqueous phase was separated and extracted twice with THF (20 mL each). The combined THF phases were concentrated to give 0.8 g of crude product, which was purified by column chromatography (eluting with 3% of MeOH in DCM) providing lapatinib with 59% HPLC purity (10 mg, 0.01 mmol).

Example 9

Synthesis of 5-(4-chloroquinazolin-6-yl)furan-2-carbaldehyde hydrochloride ((Xa).HCl)

A mixture of the compound of formula (IX) (0.6 g, 2 5 mmol), $SOCl_2$ (15 mL) and one drop of DMF was heated under reflux until the reaction was complete (TLC analysis). The volatile components were evaporated (including $SOCl_2$) to provide crude (Xa).HCl (0.9 g) that could be used directly in the next step.

Example 10

Synthesis of (IV).HCl

A mixture of (Xa).HCl (1.0 g, 2.7 mmol) and 3-chloro-4-(3-fluorobenzyloxy)aniline ((VII); 0.85 g, 3 4 mmol) in THF (20 mL) was heated at 60° C. until HPLC analysis indicated that the reaction was complete. The mixture was cooled to about 25° C. and a 2.8 N aqueous solution of NaOH (5 mL, 14 mmol) was added and was stirred. The organic layer was separated and a 2 N aqueous solution of HCl was added such that its pH value was 1-2 causing the product to precipitate. The mixture was stirred for 20 min, and was filtered and the filter cake was dried under vacuum at 40° C. to give the crude (IV).HCl (1.15 g, HPLC purity: 97.8%, 2.2 mmol, HPLC yield 78.0%).

Example 11

Synthesis of (IV).HCl

A solution of imidazole (1.4 g, 20.6 mmol), (Xa).HCl (2 g, 6.8 mmol) and 3-chloro-4-(3-fluorobenzyloxy)aniline ((VII); 1.8 g, 7 5 mmol) in DMF (20 mL, 10 P) was heated to 80±5° C. (internal temperature) with stiffing until HPLC analysis showed that the reaction was complete. A 0.5 N aqueous solution of HCl (20 mL) was added at 70-80° C. slowly causing the product to precipitate. After cooling to room temperature (25±5° C.) the mixture was filtered and washed with water (20 mL) and the filter cake was dried in vacuo at 60±5° C. for 16 h to give the crude (IV).HCl (2.85 g, 89% HPLC purity, 5.0 mmol).

Example 12

Alternative Synthesis of 5-(4-oxo-3,4-dihydroquinazolin-6-yl)furan-2-carbaldehyde ((IX))

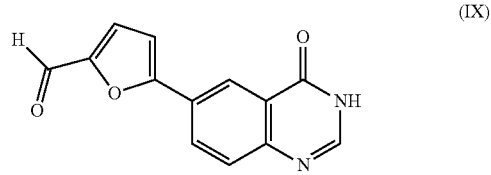 [SMILES: O=Cc1ccc(-c2ccc3nc[nH]c(=O)c3c2)o1]

(IX)

To a 40° C. solution of Na$_2$CO$_3$ (3.9 g, 36 mmol) in inert gas (nitrogen or argon) degassed aqueous dioxane (100 mL, 2:1 dioxane: H$_2$O) was added [HP(t-Bu)$_3$]BF$_4$ (0.52 g, 1.8 mmol) and Pd(OAc)$_2$ (0.4 g, 0.18 mmol). The mixture was stirred at 30° C. (internal temperature) under an atmosphere nitrogen for 30 min, and then 6-iodoquinazolin-4(3H)-one ((Va); 5 g, 18 mmol) and 5-formylfuran-2-ylboronic acid ((VIa); 4.1 g, 29 mmol) were added. The mixture was heated to 80° C. (internal temperature) and stirred until TLC analysis showed completion of the reaction. The reaction product mixture was cooled to ambient temperature and filtered through celite (1 g), and the filter cake was washed with n-BuOH (200 mL). The combined filtrates were separated and the organic layer was washed twice with a saturated aqueous solution of NaCl (100 mL each). The organic phase was concentrated down to about 50 mL under vacuum and the residue was cooled to ambient temperature with stirring to precipitate the product. The slurry was filtered and the filter cake was washed with n-BuOH (40 mL) and then dried at 60° C. under vacuum to give crude compound of formula (IX) (4.5 g, 91% HPLC, 16.5 mmol). $^1$H NMR (300 MHz, d$_6$-DMSO, 1347-126-19): δ 7.47 (d, J=3.6 Hz, 1H), 7.68 (d, J=3.6 Hz, 1H), 7.77 (d, J=8.7 Hz, 1H), 8.14 (d, J=2.1 Hz, 1H), 8.28 (dd, J=8.7 Hz, J=2.1 Hz, 1H), 8.53 (d, J=2.1 Hz, 1H), 9.64 (s, 1H).

Example 13

Synthesis of 5-(4-chloroquinazolin-6-yl)furan-2-carbaldehyde ((Xa))

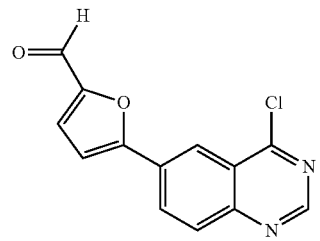

A mixture of the compound of formula (IX) (3 g, 12 5 mmol), SOCl$_2$ (30 mL) and one drop of DMF was heated at 80° C. until the reaction was complete (TLC analysis). The volatile components were evaporated (including SOCl$_2$) to provide crude compound of formula (Xa) that was purified by column chromatography (eluting with EtOAc/DCM, 1:8, v/v) to give free base of the compound of formula (Xa). The compound of formula (Xa) $^1$H NMR (300 MHz, d$_6$-DMSO): δ 7.53 (d, J=3.3 Hz, 1H), 7.68 (d, J=3.3 Hz, 1H), 8.02 (d, J=8.7 Hz, 1H), 8.42 (d, J=8.4 Hz, 1H), 8.50 (s, 1H), 8.90 (s, 1H), 9.64 (s, 1H).

TABLE 1

| | | Cross-coupling | | |
|---|---|---|---|---|
| Entry | Metal and ligand | Base | Solvent | Conversion ($^1$H NMR or HPLC) |
| 1 | Pd$_2$(dba)$_3$ (2.5 mol %) [HP(t-Bu)$_3$]BF$_4$ (5 mol %) | Na$_2$CO$_3$ (2.0 eq.) | Dioxane/H$_2$O | 100% |
| 2 | Pd(OAc)$_2$ (5 mol %) [HP(t-Bu)$_3$]BF$_4$ (5 mol %) | Na$_2$CO$_3$ (2.0 eq.) | Dioxane/H$_2$O | 100% |
| 3 | Pd(Ph$_3$P)$_4$ (5 mol %) | Na$_2$CO$_3$ (2.0 eq.) | Dioxane/H$_2$O | ca. 39% |
| 4 | Pd$_2$(dba)$_3$ (2.5 mol %) Ph$_3$P (5 mol %) | Na$_2$CO$_3$ (2.0 eq.) | Dioxane/H$_2$O | ca. 17% |
| 5 | Pd[P(t-Bu)$_3$]$_2$ (5 mol %) | Na$_2$CO$_3$ (2.0 eq.) | Dioxane/H$_2$O | ca. 38% |
| 6 | Pd(OAc)$_2$ (5 mol %) [HP(t-Bu)$_3$]BF$_4$ (10 mol %) | Na$_2$CO$_3$ (2.0 eq.) | Dioxane/H$_2$O | ca. 38% |
| 7 | Pd$_2$(dba)$_3$ (2.5 mol %) TrippyPhos (20 mol %) | Na$_2$CO$_3$ (2.0 eq.) | Dioxane/H$_2$O | ca. 11% |
| 8 | Pd(dppb)Cl$_2$ (5 mol %) | Na$_2$CO$_3$ (2.0 eq.) | Dioxane/H$_2$O | ca. 9% |
| 9 | Pd(OAc)$_2$ (1.5 mol %) [HP(t-Bu)$_3$]BF$_4$ (1.5 mol %) | Et$_3$N (1.3 eq.) | DMAC | ca. 44% |
| 10 | Pd(OAc)$_2$ (0.5 mol %) [HP(t-Bu)$_3$]BF$_4$ (0.5 mol %) | AcOK (1.3 eq.) | Dioxane/H$_2$O | ca. 90% |
| 11 | Pd(OAc)$_2$ (0.5 mol %) [HP(t-Bu)$_3$]BF$_4$ (0.5 mol %) | AcOK (1.3 eq.) | DMF/H$_2$O | ca. 90% |
| 12 | Pd(OAc)$_2$ (0.5 mol %) [HP(t-Bu)$_3$]BF$_4$ (0.5 mol %) | AcOK (1.3 eq.) | DMSO/H$_2$O | ca. 90% |
| 13 | Pd(OAc)$_2$ (1.5 mol %) [HP(t-Bu)$_3$]BF$_4$ (1.5 mol %) | AcOK (1.3 eq.) | DMAC/H$_2$O | ca. 90% |
| 14 | Pd(OAc)$_2$ (1.0 mol %) [HP(t-Bu)$_3$]BF$_4$ (1.0 mol %) | AcOK (1.3 eq.) | NMP/H$_2$O | ca. 90% |
| 15 | Pd(OAc)$_2$ (1.0 mol %) [HP(t-Bu)$_3$]BF$_4$ (1.0 mol %) | AcOK (1.3 eq.) | 2-methyl furan/H$_2$O | ca. 79% |
| 16 | Pd(OAc)$_2$ (1.0 mol %) [HP(t-Bu)$_3$]BF$_4$ (1.0 mol %) | AcOK (1.3 eq.) | MeCN/H$_2$O | ca. 90% |

The invention claimed is:

1. A process for preparing lapatinib or its pharmaceutically acceptable salt, comprising converting a compound of formula (IX):

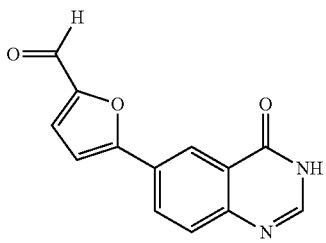

(IX)

to lapatinib or its pharmaceutically acceptable salt.

2. The process of claim 1 wherein the step of converting the compound of formula (IX) comprises:
   i) activating the compound of formula (IX) with a halogenating, sulfonating, phosphonylating or amide bond-forming reagent;
   ii) reacting the activated compound of formula (IX) with 3-chloro-4-(3-fluorobenzyloxy)aniline (VII) to produce the compound of formula (IV) or its salt

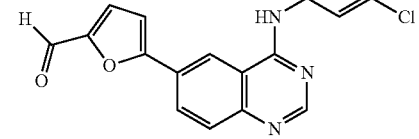

(IV)

and
   iii) converting the compound of formula (IV) or its salt to lapatinib or its pharmaceutically acceptable salt.

3. The process of claim 2, wherein the halogenating reagent is a chlorinating agent.

4. The process of claim 3, wherein the chlorinating agent is selected from the group consisting of $SOCl_2$, $POCl_3$, $(COCl)_2$, $PCl_3$, $PCl_5$, and $COCl_2$.

5. The process of claim 2, wherein step ii) is conducted in the presence of a palladium-based or copper-based catalyst.

6. The process of claim 1, comprising:
   i) reacting the compound of formula (IX) with 2-(methylsulfonyl)ethanamine ((VIII)) or its salt to produce the compound of formula (XI);
   ii) activating the compound of formula (XI) with an activating agent to produce the compound of formula (XII); and
   iii) converting the compound of formula (XII) into lapatinib by reaction of the compound of formula (XII) with the compound of formula (VII).

7. A process for the preparation of lapatinib ditosylate monohydrate crystals comprising the steps of:
   i) dissolving lapatinib ditosylate in dimethyl sulfoxide (DMSO) at a raised temperature,
   ii) optionally conducting a filtration operation on the solution of dissolved lapatinib ditosylate,
   iii) adding a mixture of acetonitrile (MeCN) and water to the dimethyl sulfoxide (DMSO) solution of lapatinib ditosylate at a raised temperature,
   iv) cooling the solution such that lapatinib ditosylate monohydrate crystallizes, and
   v) isolating the lapatinib ditosylate monohydrate crystals.

8. The process of claim 7 where the raised temperature is between 65-80° C. such that the acetonitrile (MeCN) does not boil, but such that the lapatinib ditosylate monohydrate does not crystallise.

9. A process for preparing a compound of formula (IX):

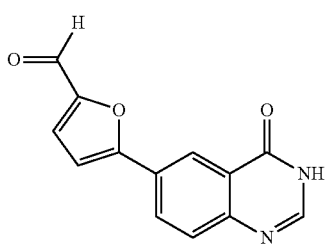

(IX)

comprising a step of reacting a compound of formula (V):

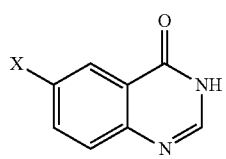

(V)

wherein X is halogen; with a compound of formula (VI):

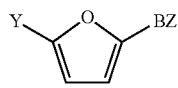

(VI)

wherein
BZ is $B(OH)_2$, $B(OR)_2$, or $[BF_3]M$, $BR_2$;
Y is CH=O or $CH(OR)_2$;
$CH(OR)_2$ and $B(OR)_2$ are cyclic or acyclic;
$B(OR)_2$ can be a boronic anhydride;
R is alkyl, aryl, heteroaryl, or allyl;
M is metal ion;
in the presence of an effective amount of catalyst, base and solvent.

10. The process of claim 9 wherein X is I.

11. The process of claim 9 wherein the compound of formula (VI) is of formula (VIa), or its boronic anhydride form,

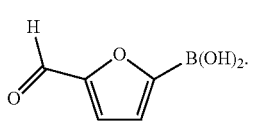

(VIa)

12. The process of claim 9 wherein the catalyst is comprised from a phosphine ligand with a transition metal or transition metal salt.

13. The process of claim 12 wherein the transition metal or transition metal salt is palladium or a palladium salt.

14. The process of claim 12 wherein the phosphine ligand is P(t-Bu)$_3$ or its salt derivative.

15. The process of claim 14 wherein the salt derivative is [HP(t-Bu)$_3$]BF$_4$.

16. The process of claim 9 wherein the base is a hydroxide, an alkoxide, a metal carbonate, metal bicarbonate, an amine, a metal carboxylate or a metal phosphate.

17. The process of claim 16 wherein the metal carbonate is Na$_2$CO$_3$.

18. The process of claim 16 wherein the metal carboxylate is AcOK.

19. The process of claim 9 wherein the solvent is a mixture of water with dimethyl sulfoxide (DMSO), N,N-dimethylformamide (DMF), N,N-dimethylacetamide (DMAC), N-methylprrolidone (NMP), acetonitrile (MeCN), 1,4-dioxane or 2-methyl furan.

20. The process of claim 19 wherein the solvent is a mixture of water and dimethyl sulfoxide (DMSO).

21. The process of claim 20, wherein the ratio of dimethyl sulfoxide (DMSO) to H$_2$O is 5:2.

22. The process of claim 9, where the following steps are conducted on the compound of formula (IX) that is dissolved in the crude reaction product solution:
  i) hot filtering the dissolved compound of formula (IX) at a temperature such that the reaction product of formula (IX) remains dissolved in solution,
  ii) adding hot water to the hot filtrate containing the compound of formula (IX),
  iii) cooling the solution to crystallise the compound of formula (IX), and
  iv) isolating the compound of formula (IX).

23. The process of claim 9, where the reacting is conducted at a temperature between 60-95° C.

24. A compound of formula (IX):

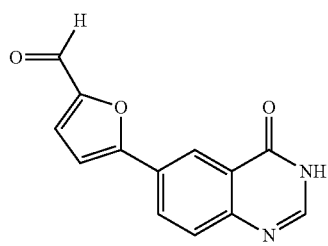

(IX)

25. A crystalline form of a compound of formula (IX):

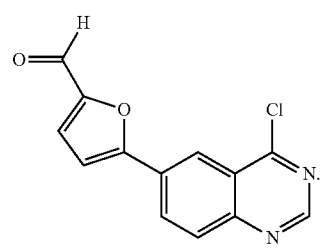

(IX)

exhibiting an X-ray powder diffraction pattern comprising the following peaks: 4.38, 12.65, 13.34, and 15.59 in two theta±0.2.

26. A compound of formula Xa:

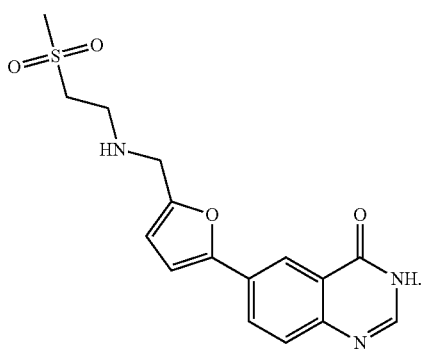

(Xa)

27. A compound of formula (XI):

(XI)

* * * * *